(12) United States Patent
Nebosis et al.

(10) Patent No.: US 9,551,565 B2
(45) Date of Patent: Jan. 24, 2017

(54) METHOD AND SYSTEM FOR OPTICAL COHERENCE TOMOGRAPHY INCLUDING OBTAINING AT LEAST TWO TWO-DIMENSIONAL IMAGES OF AN OBJECT IN THREE-DIMENSIONAL SPACE

(75) Inventors: Rainer Nebosis, Munich (DE); Roland Reuter, Kolbermoor (DE)

(73) Assignee: AGFA HEALTHCARE NV, Mortsel (BE)

( * ) Notice: Subject to any disclaimer, the term of this patent is extended or adjusted under 35 U.S.C. 154(b) by 120 days.

(21) Appl. No.: 14/009,379

(22) PCT Filed: Mar. 30, 2012

(86) PCT No.: PCT/EP2012/001436
§ 371 (c)(1),
(2), (4) Date: Oct. 28, 2013

(87) PCT Pub. No.: WO2012/136339
PCT Pub. Date: Oct. 11, 2012

(65) Prior Publication Data
US 2014/0049781 A1   Feb. 20, 2014

(30) Foreign Application Priority Data
Apr. 6, 2011 (EP) .................... 11002894

(51) Int. Cl.
*G01B 9/02* (2006.01)
*A61B 5/00* (2006.01)
*G01N 21/47* (2006.01)

(52) U.S. Cl.
CPC ......... *G01B 9/02091* (2013.01); *A61B 5/0066* (2013.01); *A61B 5/0073* (2013.01); *A61B 5/444* (2013.01); *G01B 9/02063* (2013.01); *G01B 9/02085* (2013.01); *G01B 9/02089* (2013.01); *G01N 21/4795* (2013.01); *A61B 2560/0437* (2013.01); *A61B 2562/0233* (2013.01)

(58) Field of Classification Search
CPC ............ G01B 9/02091; G01B 9/02089; G01B 9/02085; G01B 9/02063; A61B 5/0066; A61B 5/0073; A61B 5/444; A61B 2560/0437; A61B 2562/0233; A61B 3/102; A61B 5/0033; A61B 5/0035; A61B 2019/5234; G01N 21/4795
See application file for complete search history.

(56) References Cited

U.S. PATENT DOCUMENTS 5,368,033 A * 11/1994 Moshfeghi .................... 600/419
2003/0103212 A1* 6/2003 Westphal et al. ............. 356/479
(Continued)

*Primary Examiner* — Michael P Lapage
(74) *Attorney, Agent, or Firm* — Keating and Bennett, LLP

(57) ABSTRACT

A method and corresponding system for optical coherence tomography includes optical coherence tomography equipment that acquires at least two two-dimensional initial images of an object in planes of the object that are spaced apart from one another, in particular running parallel to one another, wherein the initial images each include a plurality of initial image values. In order to assure an examination of the object in the case of medical applications that is as reliable as possible, an interpolation of the initial image values of the at least two two-dimensional initial images is performed in three-dimensional space, wherein interpolation values are obtained that form a two-dimensional final image.

17 Claims, 19 Drawing Sheets

(56) References Cited

U.S. PATENT DOCUMENTS

Figure 1:
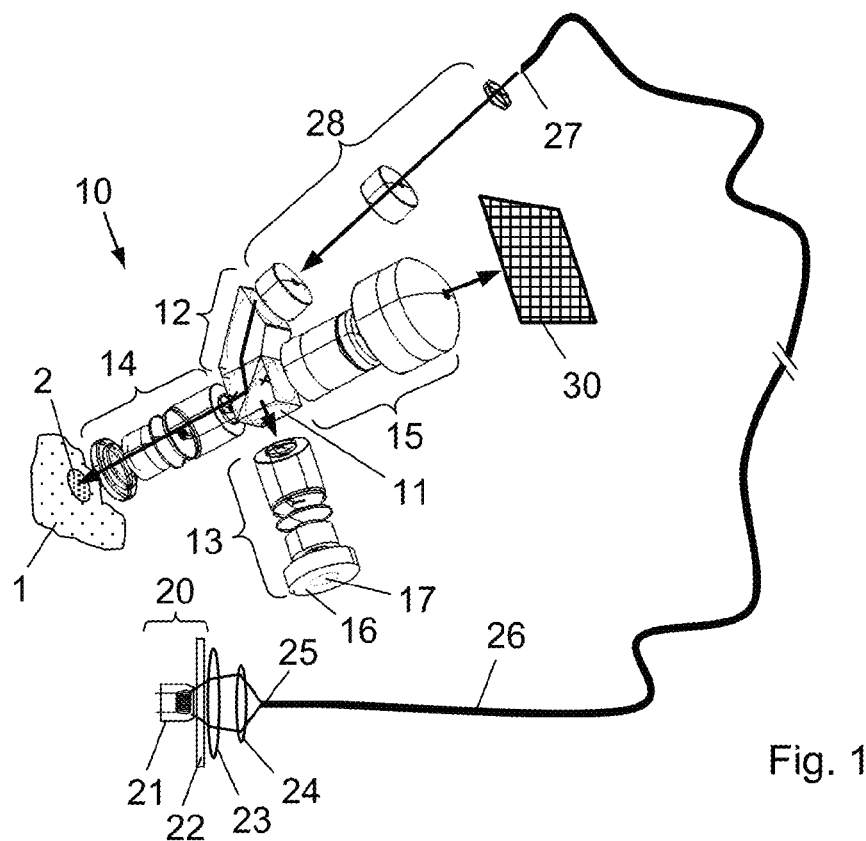

| | | | |
|---|---|---|---|
| 2007/0291277 A1* | 12/2007 | Everett et al. | 356/497 |
| 2008/0151187 A1* | 6/2008 | Tsukada et al. | 351/206 |
| 2008/0175465 A1* | 7/2008 | Jiang et al. | 382/131 |
| 2011/0267340 A1* | 11/2011 | Kraus | A61B 3/102 345/419 |
| 2013/0156283 A1* | 6/2013 | Beg et al. | 382/131 |

* cited by examiner

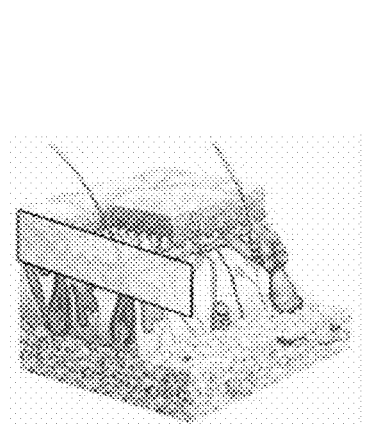
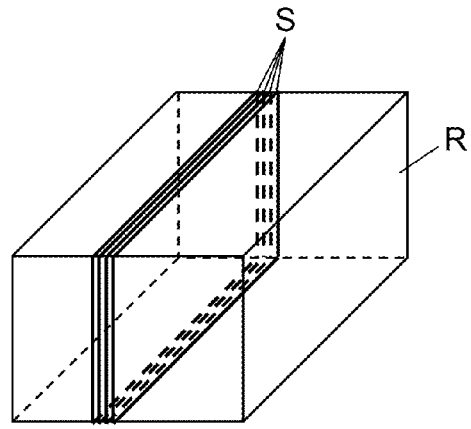
Fig. 3
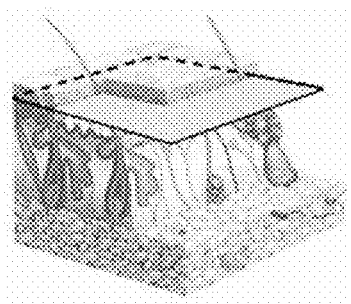
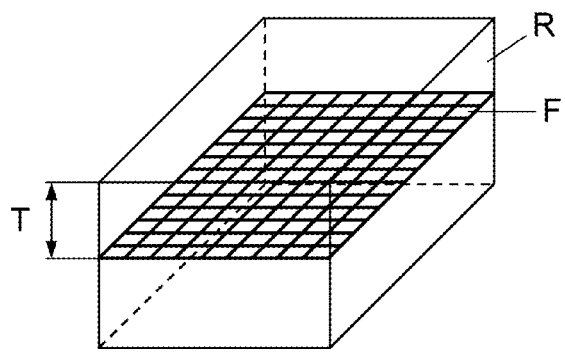
Fig. 4
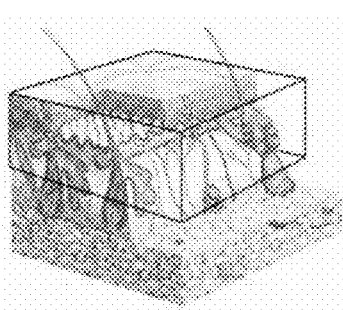
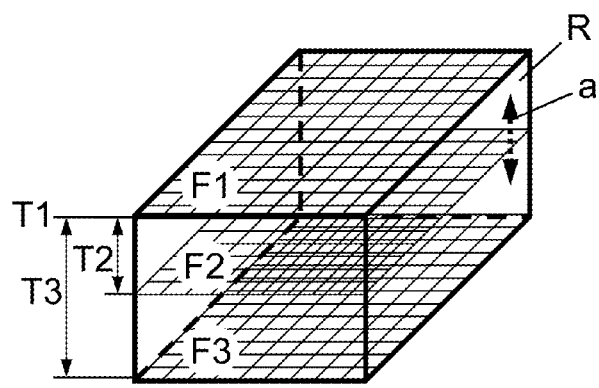
Fig. 5

METHOD AND SYSTEM FOR OPTICAL COHERENCE TOMOGRAPHY INCLUDING OBTAINING AT LEAST TWO TWO-DIMENSIONAL IMAGES OF AN OBJECT IN THREE-DIMENSIONAL SPACE

The present invention relates to a method and a corresponding system for optical coherence tomography.

Optical coherence tomography (OCT) is a method of measuring light-scattering specimens on their inside. Due to its light-scattering properties biological tissue is particularly suitable for diagnostic examination by means of OCT. Since for OCT relatively low light intensities are sufficient and the wavelengths of the light used mostly come within the near infrared range (750 nm to 1350 nm), unlike ionising X-ray diagnostics it does not contaminate biological tissue with radiation. It is therefore particularly significant for medicine and is roughly comparable to ultrasound diagnostics, wherein with OCT, light is used instead of sound. The running times of the light reflected on different boundary layers within the specimen are recorded with the aid of an interferometer. With OCT, typically resolutions higher by one to two orders of magnitude are to be achieved than with ultrasound, but the measuring depth achievable is considerably smaller. Due to optical scattering the cross-section images obtained usually only reach into the tissue up to a depth of a few millimeters. The currently most important areas of application of OCT are in ophthalmology, dermatology and the diagnosis of cancer. However, there are also some non-medical applications, such as e.g. in materials testing.

In particular in medical applications of OCT special demands are placed on methods and systems to ensure an examination of the object which is as reliable as possible.

The object of the present invention is to specify a method as well as a corresponding system for optical coherence tomography that permits a reliable examination of an object.

The aforesaid object is achieved by the method and the system according to the independent claims.

In the context of the inventive method for optical coherence tomography, at least two two-dimensional initial images of an object are acquired by means of an optical coherence tomography equipment in planes of the object that are spaced apart from one another, in particular running parallel to one another, wherein the initial images each comprise a plurality of initial image values, in particular intensity values. Furthermore an interpolation of the initial image values of the at least two two-dimensional initial images in three-dimensional space is performed, wherein interpolation values are obtained that form a two-dimensional final image.

The inventive system for optical coherence tomography comprises an optical coherence tomography equipment for the acquisition of at least two two-dimensional initial images of an object in planes of the object that are spaced apart from one another, in particular running parallel to one another, wherein the initial images each comprise a plurality of initial image values, in particular intensity values, and said system is characterized by a processing device for the interpolation of the initial image values of the at least two two-dimensional initial images in three-dimensional space, wherein interpolation values are obtained that form a two-dimensional final image.

The invention is based on the concept of initially acquiring two initial section images in two parallel running planes of the object with the optical coherence tomography equipment, and to then interpolate the initial image values of the two initial section images in three-dimensional space, which is spanned by the two initial section images that are spaced apart from one another, in such a way that a two-dimensional final section image is obtained from interpolation values, i.e. interpolated initial image values. For the derivation of the interpolation values initial image values of not only one but both initial section images are hereby interpolated. In so doing, an interpolation value is derived from at least one initial image value of a first initial section image, and at least one initial image value from a second initial section image. For example, an interpolation value is derived from eight initial image values, wherein four initial image values originate from the first initial section image and four initial image values originate from the second initial section image.

In the case of the OCT images obtained with the inventive method and system, cavities or other structures of a scale larger than approximately 10 μm appear more clearly than is the case in the respective initial section images. However, also smaller structures can be identified and, if necessary, examined more reliably and faster. Particularly in the area of dermatology certain diagnostically relevant and interesting structures of the skin can as a result be recognized and examined with particularly high reliability.

Preferably the respective initial section images, whose initial image values are determined by inventive means, are acquired simultaneously or almost simultaneously, in particular temporally spaced less than 40 milliseconds apart, preferably less than 20 milliseconds.

Initial section images are simultaneously acquired, for example, during an acquisition of initial images in the form of depth sections, so-called slices, in a first operating mode, which is described in further detail below.

The almost simultaneous acquisition of initial section images, for the purposes of the invention, takes place, for example, during an acquisition of initial images in the form of two-dimensional tomograms, so-called en-face images, in a second operating mode, which is described in further detail below.

A simultaneous or nearly simultaneous acquisition of initial section images can however also be performed by acquiring a complete three-dimensional data set of the object in a third operating mode, which is described in further detail below.

The simultaneous or almost simultaneous acquisition of the initial section images to be averaged has the advantage that the effect of possible temporal changes of the object being examined on the final image, which is obtained by the averaging process, is eliminated or significantly reduced, which increases the accuracy and reliability of the images that are obtained during the examination of the object.

Preferably the initial image values of the at least two two-dimensional initial images are located on a regular grid in three-dimensional space, wherein adjacent initial image values in all three spatial dimensions are equally spaced apart, in particular between approximately 2 μm and 4 μm. As a result the inventive interpolation of the initial image values of the two initial images can be realized in a straightforward manner.

Further preferred is that the initial image values of the at least two two-dimensional initial images are interpolated by means of a trilinear interpolation and/or a tricubic interpolation. The trilinear or tricubic interpolation concerns a method for the interpolation within a three-dimensional regular grid, i.e. a grid with the same grid constant in all three spatial directions, wherein an interpolation value located in the center point of the respective grid cells of the grid is determined through linear or cubic interpolation from respectively eight initial image values, which are located at the eight corners of the grid cell. The initial image values located at the eight corners of the grid cell represent the next neighbors of the respective interpolation value, which is why the trilinear or tricubic interpolation can also be regarded as a next neighbor interpolation. Final images of particular high diagnostic assessment value are obtained by means of this type of interpolation.

A quadratic interpolation can also be performed instead of or in addition to a linear or cubic interpolation of the initial image values of next neighbors. In this case the initial image values of the at least two two-dimensional initial images are interpolated using a triquadratic interpolation.

Preferably the at least two two-dimensional initial images of the object are real time images that are acquired at a rate of at least one image per second, preferably at least five images per second. This is advantageously possible, since the inventive interpolation represents a straightforward and very fast method that can be applied without temporal delay to OCT images acquired in real time. In this manner initial images acquired in real time can also be rendered in real time, i.e. with a corresponding image repetition rate, in the form of inventively interpolated final images, with diagnostic information that can correspondingly be comprehended better, on a corresponding display device.

In an additional advantageous embodiment of the invention the at least two two-dimensional initial images of the object are acquired, in a first operating mode, in planes of the object that are spaced apart from one another, where light reflected or backscattered by the object is detected only by a partial surface, in particular by two adjacent lines, of a spatially resolving detector of the optical coherence tomography equipment, while the optical distance of a reflector from a beam splitter of the optical coherence tomography equipment is changed by an optical path that is significantly larger, in particular at least 100 times, than the mean wavelength of light injected into the optical coherence tomography equipment. This operating mode permits the acquisition of initial images in the form of depth sections, so-called slices, at high speed and consequently in real time, i.e. at a rate of at least one image per second, in a straightforward manner and with high reliability. The increased diagnostic assessment value of the real time images captured and interpolated in this manner enables an even more reliable examination of the object.

In a further, likewise preferred, embodiment of the invention the at least two two-dimensional initial images of the object are acquired, in a second operating mode, in planes of the object that are spaced apart from one another, where during a changing of the optical distance of a reflector from a beam splitter of the optical coherence tomography equipment the light reflected from the object is detected several times, in particular at most five times, by detector elements of a detector, wherein the change of the optical distance of the reflector from the beam splitter is at most forty times the mean wavelength of light injected into the optical coherence tomography equipment. In this operating mode initial images in the form of two-dimensional tomograms, so-called en-face images, can be acquired with a high repetition rate, in particular in real time. The increased diagnostic assessment value of the real time images captured and interpolated in this manner facilitates, in the context of this embodiment also, an even more reliable examination of the object.

In this case the two planes of the object run preferably at different depths above and below a mean depth in the object. In particular the two planes of the object run at the same spacing above and below the mean depth in the object. Preferably the spacing of the two planes relative to one another corresponds hereby to the same spacing of the initial image values in all three spatial directions. These measures assure the determination of the interpolation values with particularly high reliability.

In a further advantageous improvement of the invention the mean depth or the different depths of the planes running above and below the mean depth in the object is (are) set by the distance of the reflector from the beam splitter. Preferably the optical distance of the reflector from the beam splitter of the optical coherence tomography equipment is hereby changed by an optical path that is significantly larger, in particular at least 100 times, than the mean wavelength of the light injected into the optical coherence tomography equipment. The acquisition of the initial images in the form of en-face images at different planes of the object can thereby be realized in a straightforward and quick manner.

In another preferred embodiment provision is made that prior to performing the interpolation the plurality of original initial image values of the at least two two-dimensional initial images is reduced at least in one dimension, in particular in the direction of the depth of the object, by combining respectively at least two, preferably more than ten, original initial image values to one initial image value. In particular, the original initial image values concern sampling values that are obtained by the successive sampling of an interference pattern that is obtained from different depths within a depth range of the object. In this process preferably those original initial image values are combined that are obtained from the range, in particular the depth range, of the object whose extent in the at least one dimension corresponds to the resolution, in particular the axial resolution or depth resolution, of the optical coherence tomography equipment.

These measures on the one hand take into consideration that the sampling of the interference signal must be high enough so as not to violate the so-called sampling theorem. On the other hand the fact is thereby also taken into account that the spacing between two sampling values of the interference signal is generally significantly smaller than the physical resolution of the imaging optics of the optical coherence tomography equipment. This means that several, preferably more than ten, sequentially following sampling values contain approximately the same physical information, and can therefore be combined into one value without significant loss of information. The initial image value corresponds thereby, for example, to a mean value or the median of the original initial image values. As a result the captured data volume in the form of the original initial image values is significantly reduced without significant loss of information, and furthermore the equal spacings of the initial image values in all three spatial directions, which are required for a particularly reliable execution of the interpolation, can be straightforwardly implemented.

Furthermore preferred is that the depth of field of the imaging optics of the optical coherence tomography equipment is larger than the spatial distance, which preferably is identical in all three spatial directions, of the initial image values from one another. As a result the initial images and the final images obtained through interpolation thereof are always captured or obtained with the required accuracy.

Figure 2:
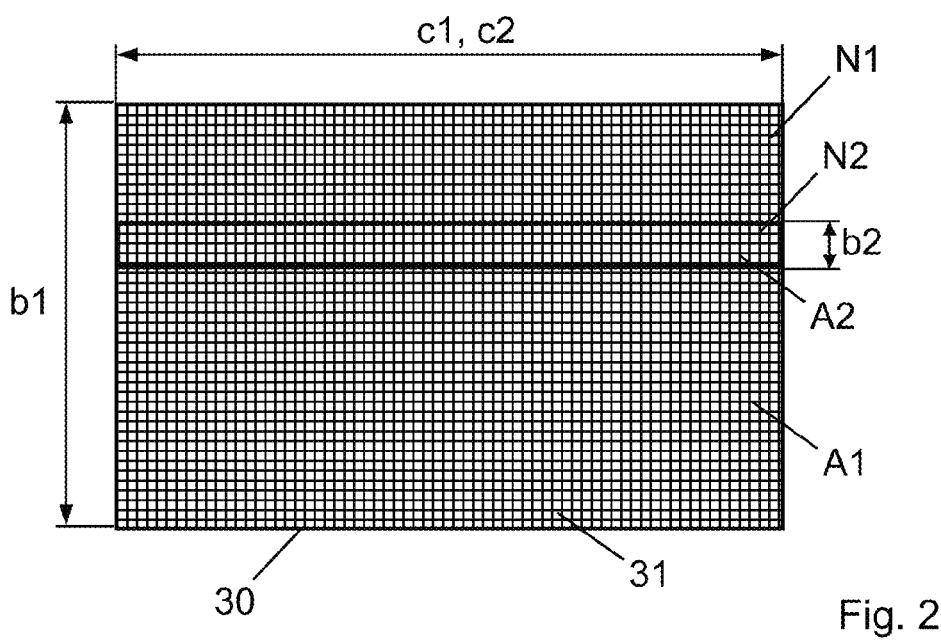
Figure 7:
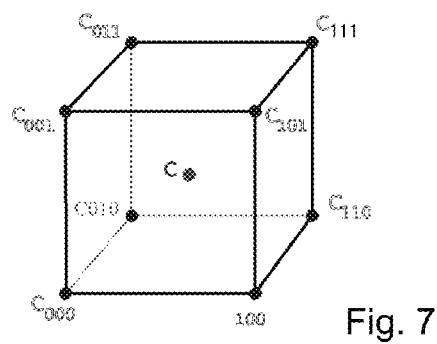
Figure 8:
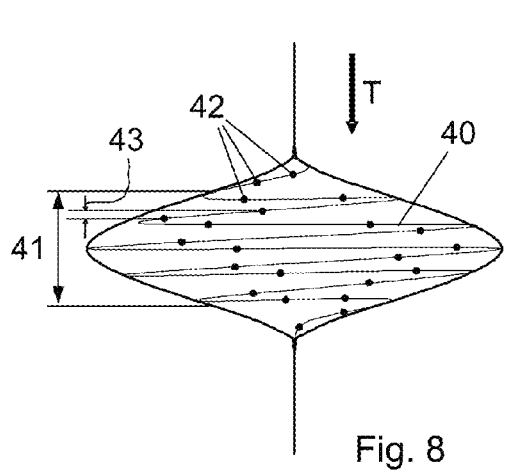
Figure 9:
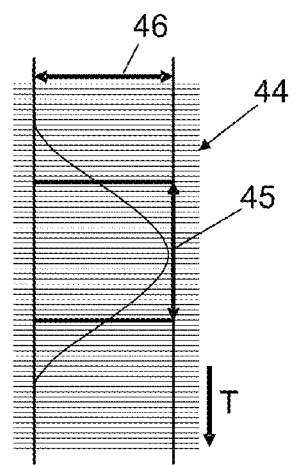
Figure 10:
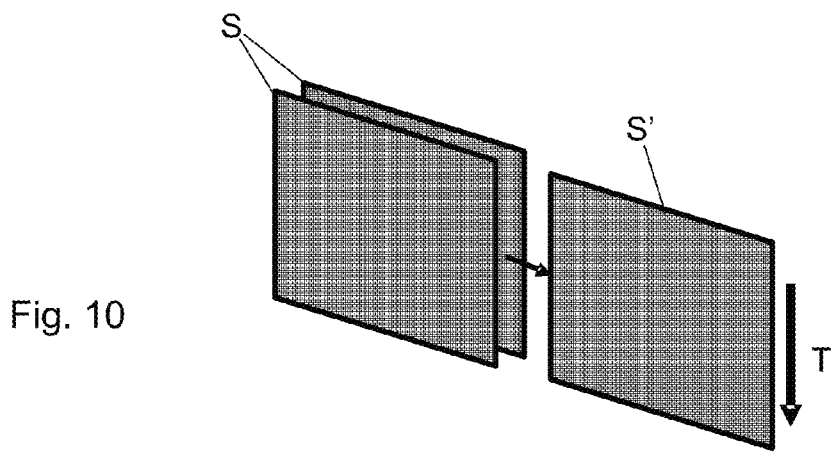
Figure 11:
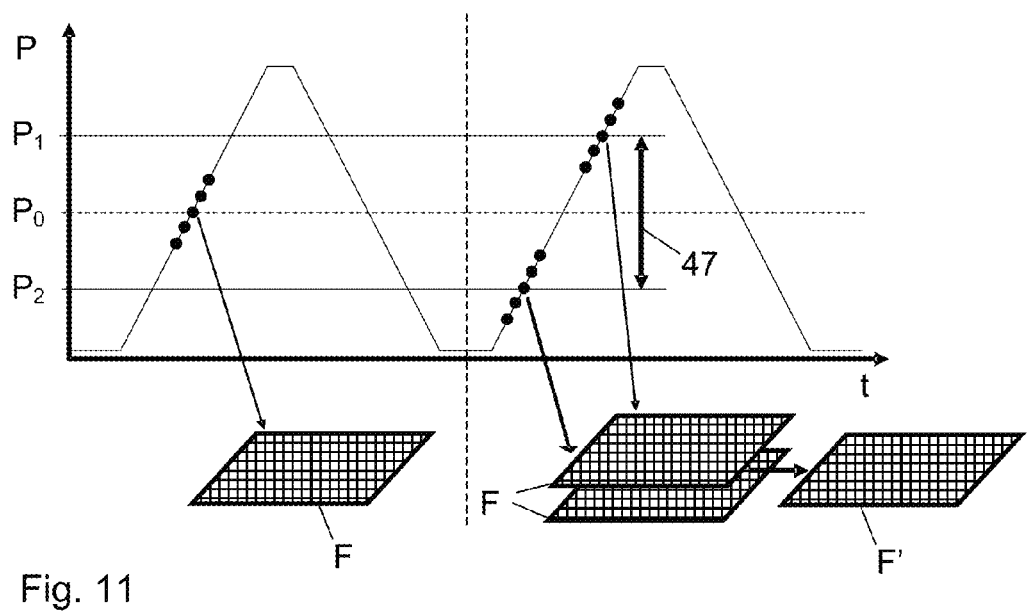

Additional advantages, features and possible applications of the present invention are specified in the following description in the context of the figures. The drawings show:

FIG. 1 a schematic representation of an example of an optical coherence tomography equipment;

FIG. 2 a schematic representation of an example of a detector surface for illustrating a first operating mode;

FIG. 3 a spatial element of the object with cuts in first planes for the illustration of the first operating mode;

FIG. 4 a spatial element of the object with a cut in a second plane for the illustration of a second operating mode;

FIG. 5 a spatial element of the object with cuts in second planes for the illustration of the third operating mode;

FIG. 6 a) and b) two cross sections through the object and the sample arm of the interferometer for the illustration of the focus tracking;

FIG. 7 an example of a regular grid for the illustration of the interpolation of initial image values;

FIG. 8 a schematic view for illustrating a sampling of an interference pattern in the direction of the depth of an object in comparison to the physical resolution in the direction of the depth;

FIG. 9 an additional schematic view for illustrating a compilation of original initial image values, sampled in the direction of the depth of an object, relative to respectively one initial image value in comparison to the physical resolution in the direction of the depth;

FIG. 10 an additional schematic view for the illustration of the interpolation of the initial image values from two initial images obtained in the direction of the depth of the object;

FIG. 11 an additional schematic view for the illustration of the acquisition of the initial image values in one (left) or two (right) planes that are transversal to the direction of the depth of an object, as well as the interpolation of the initial image values of the initial images obtained from the two planes (right).

Figure 12:
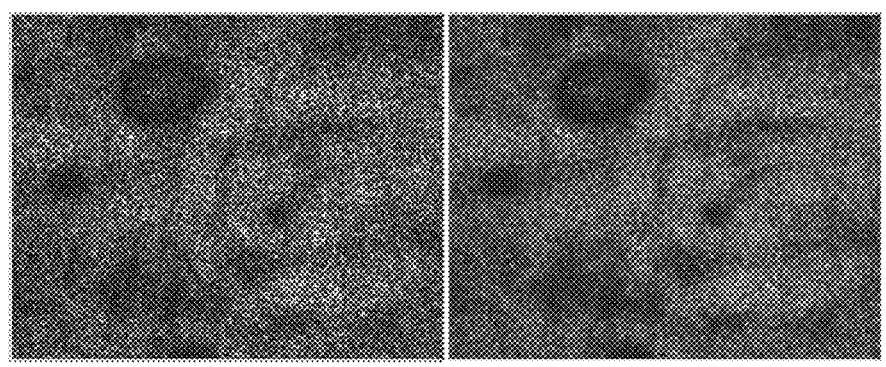
Figure 13:
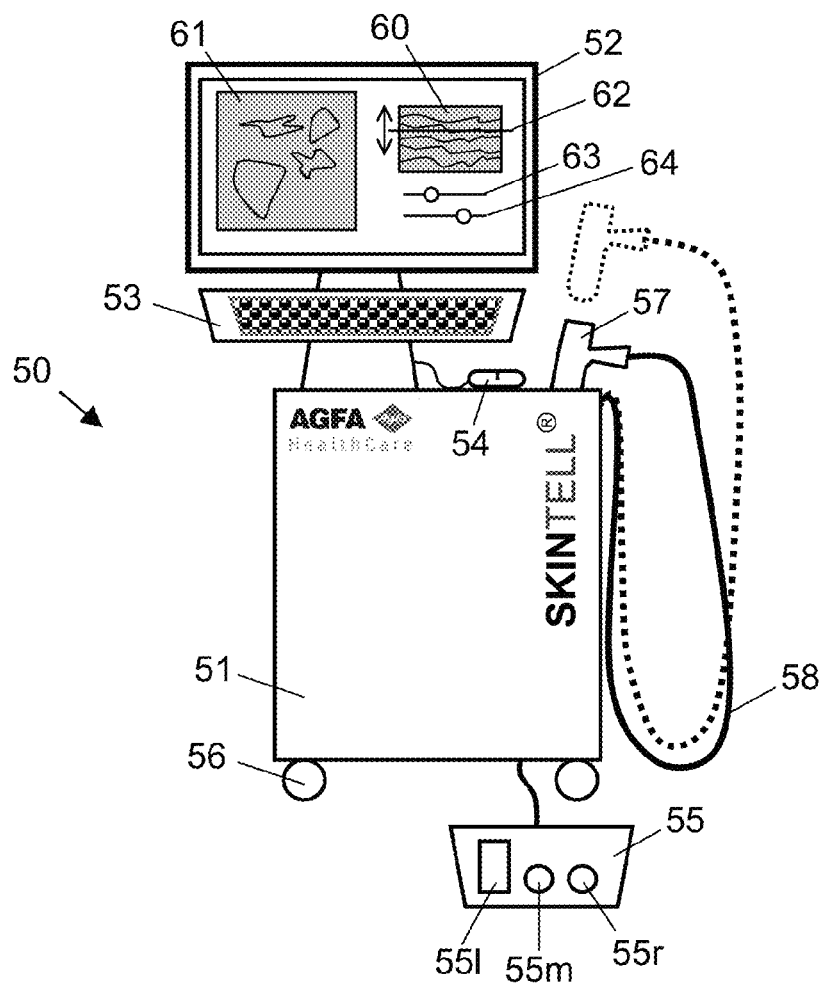
Figure 14:
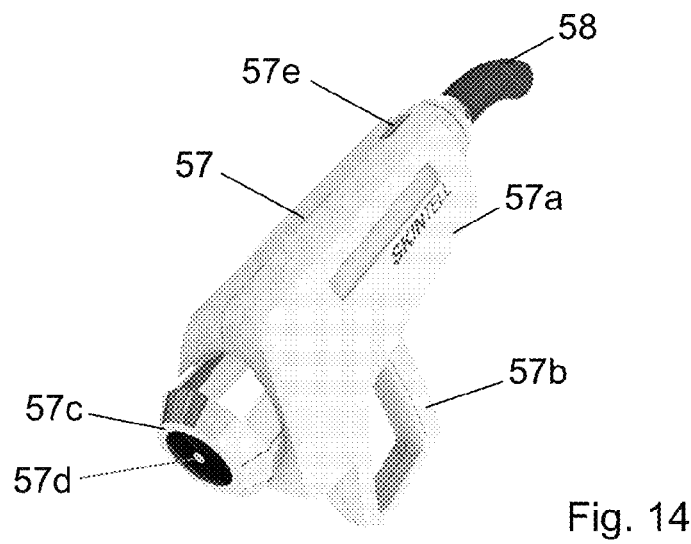
Figure 15:
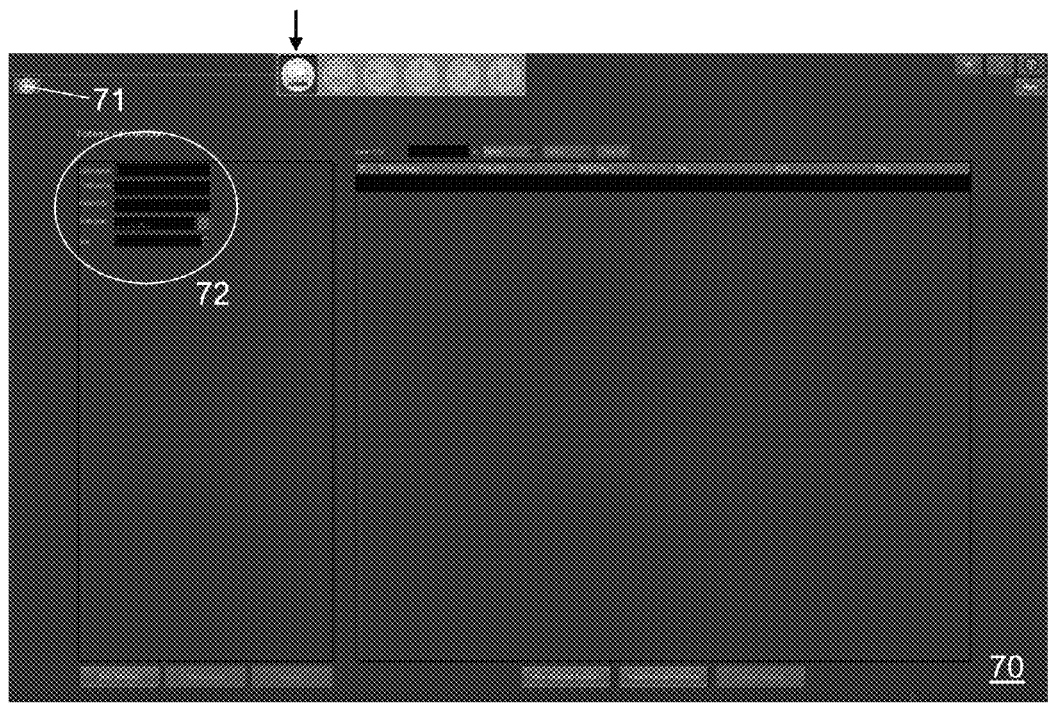
Figure 16:
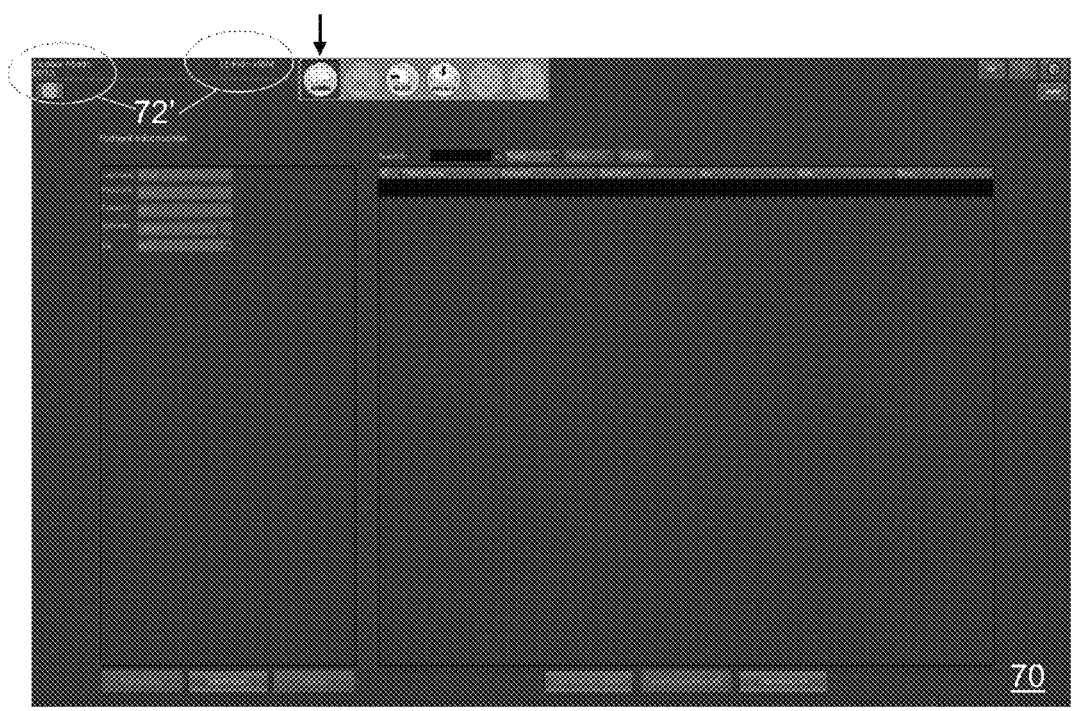
Figure 17:
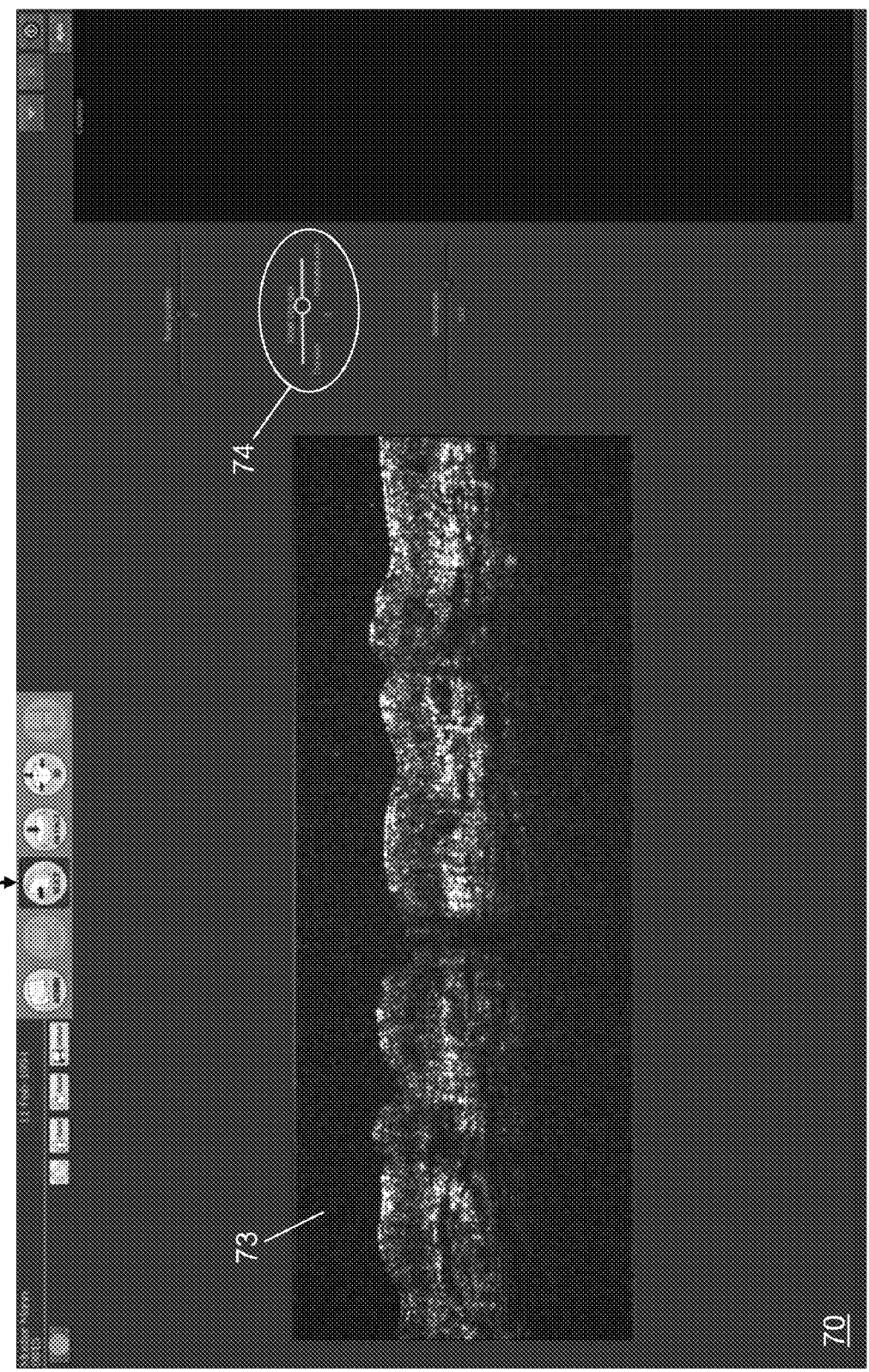
Figure 18:
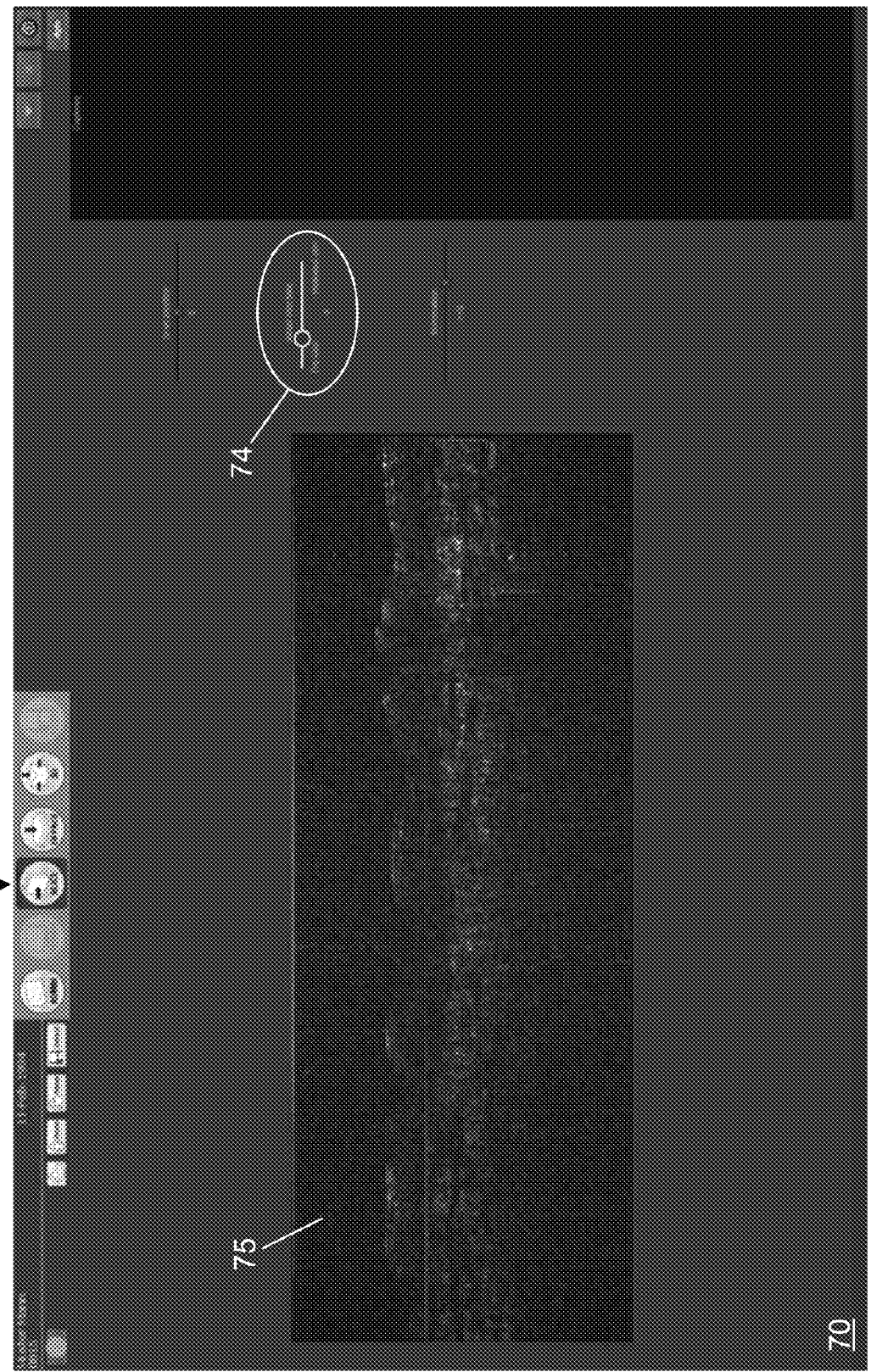
Figure 19:
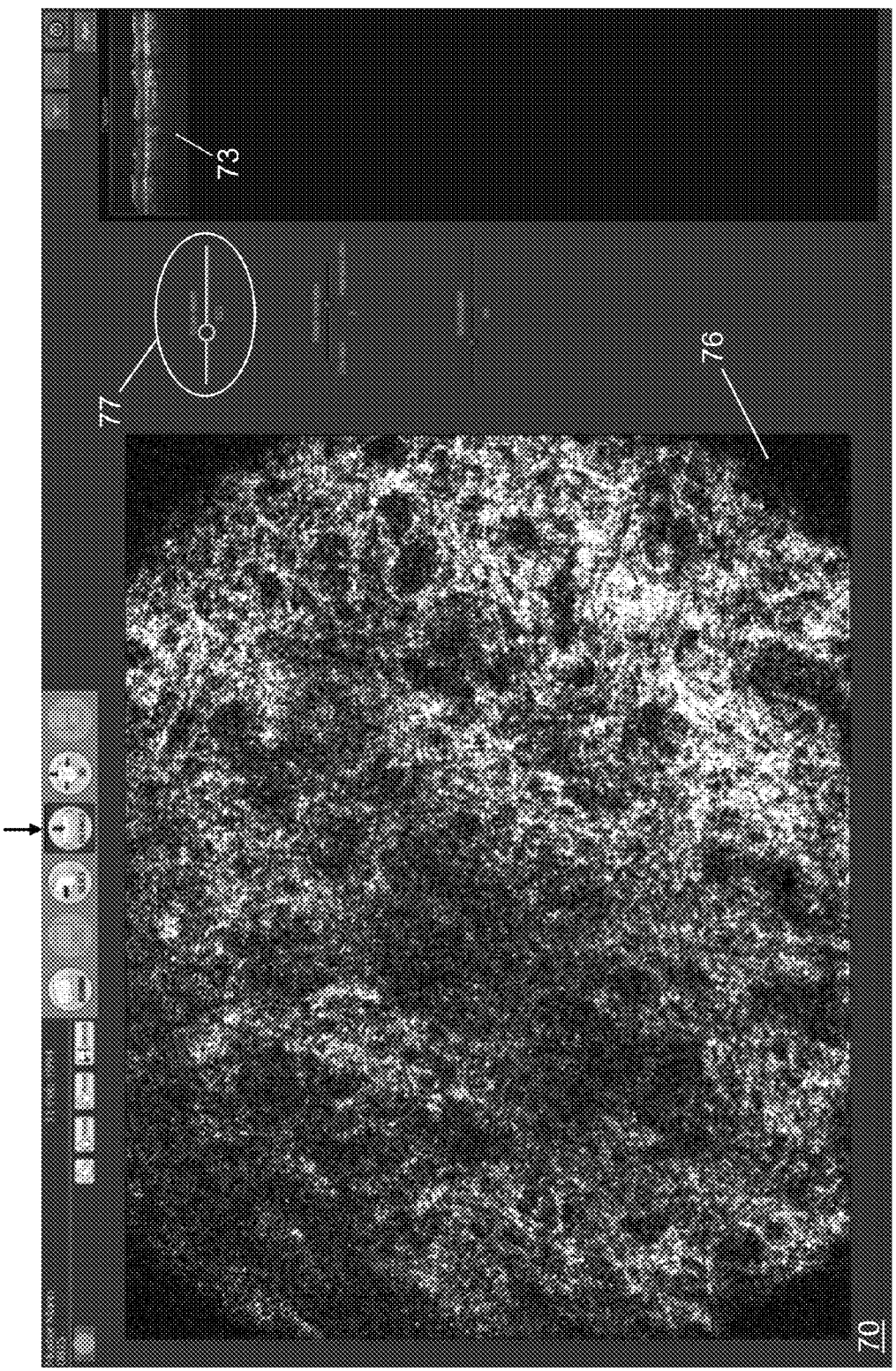
Figure 20:
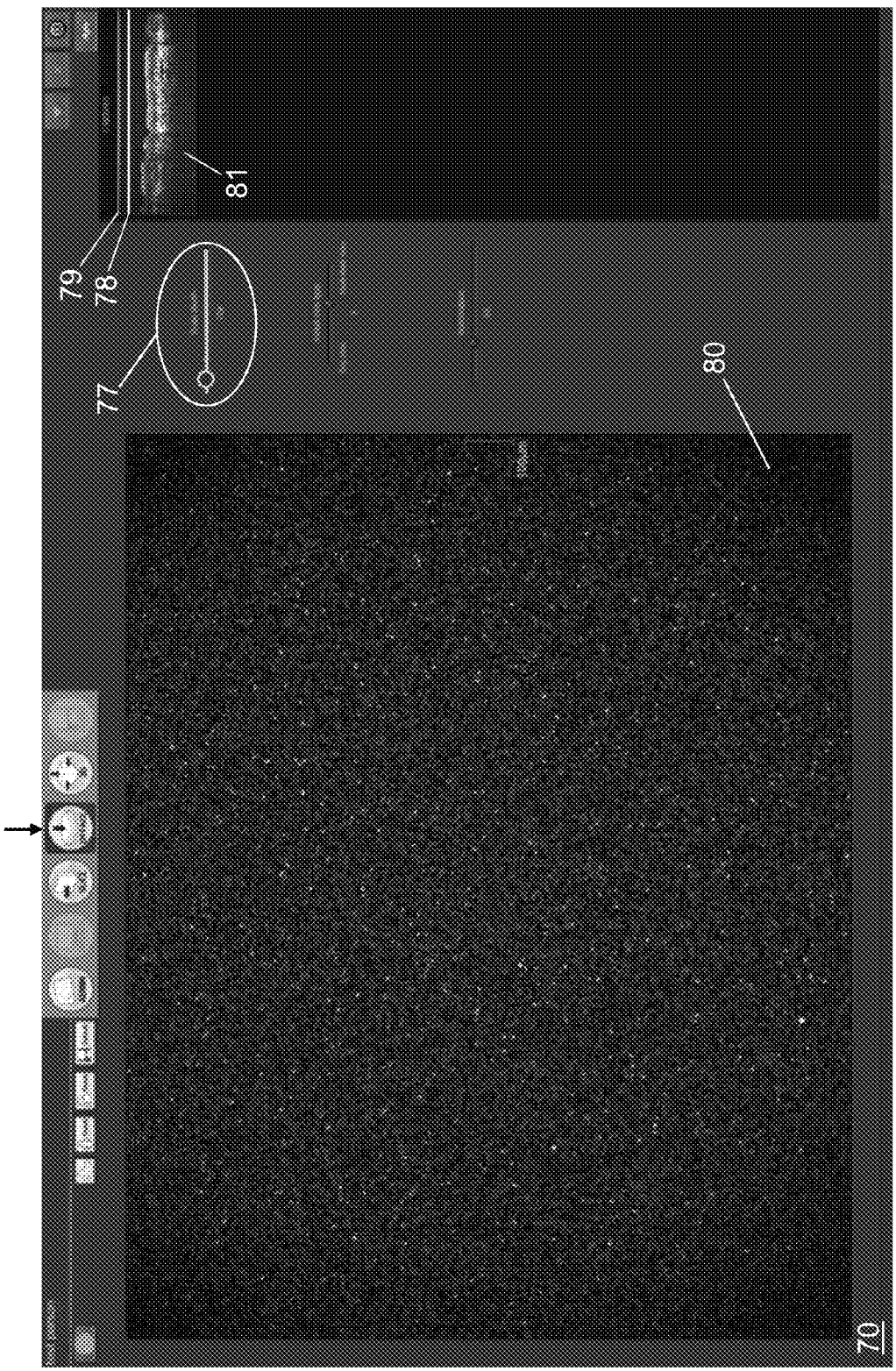
Figure 21:
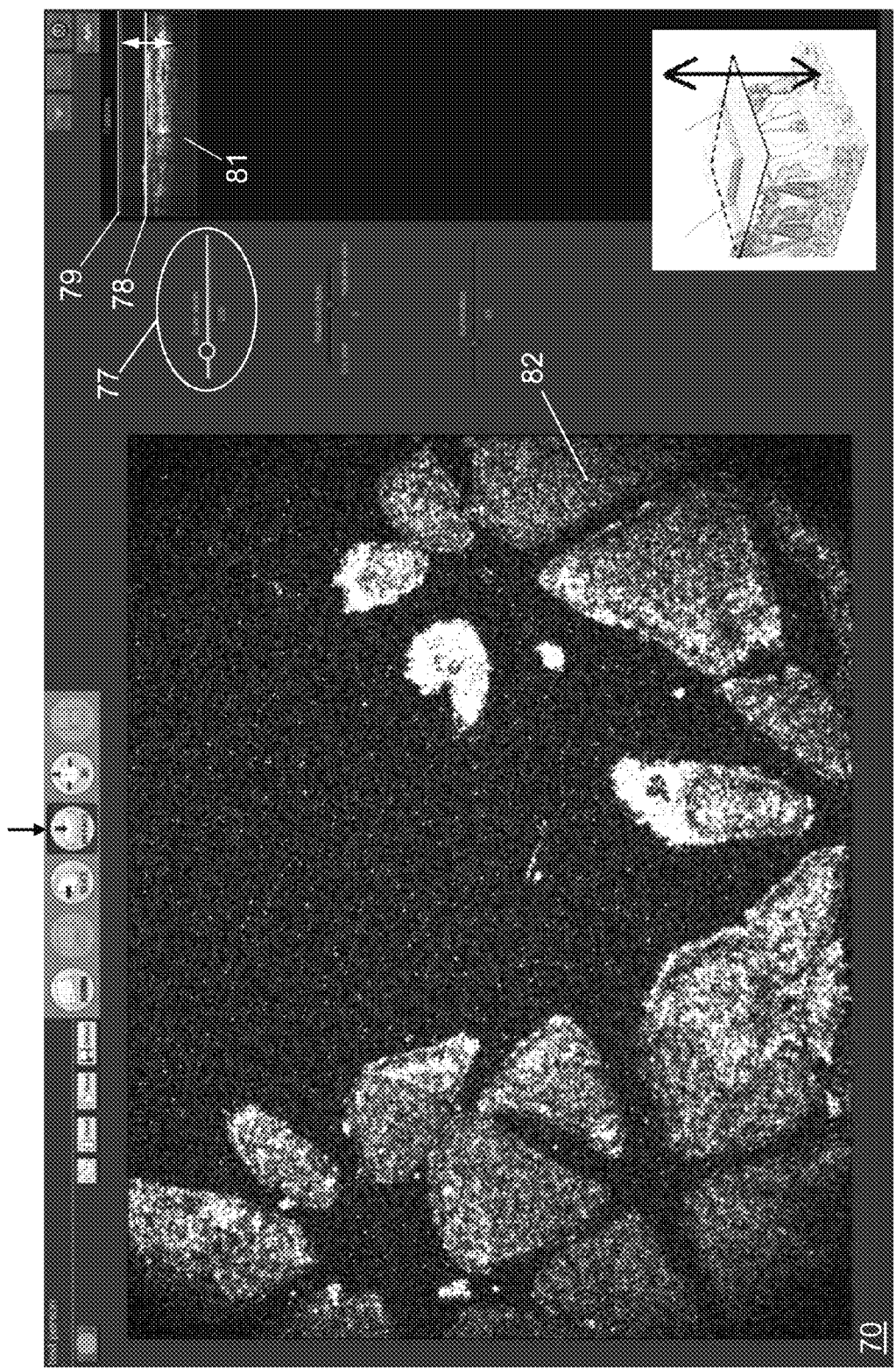
Figure 22:
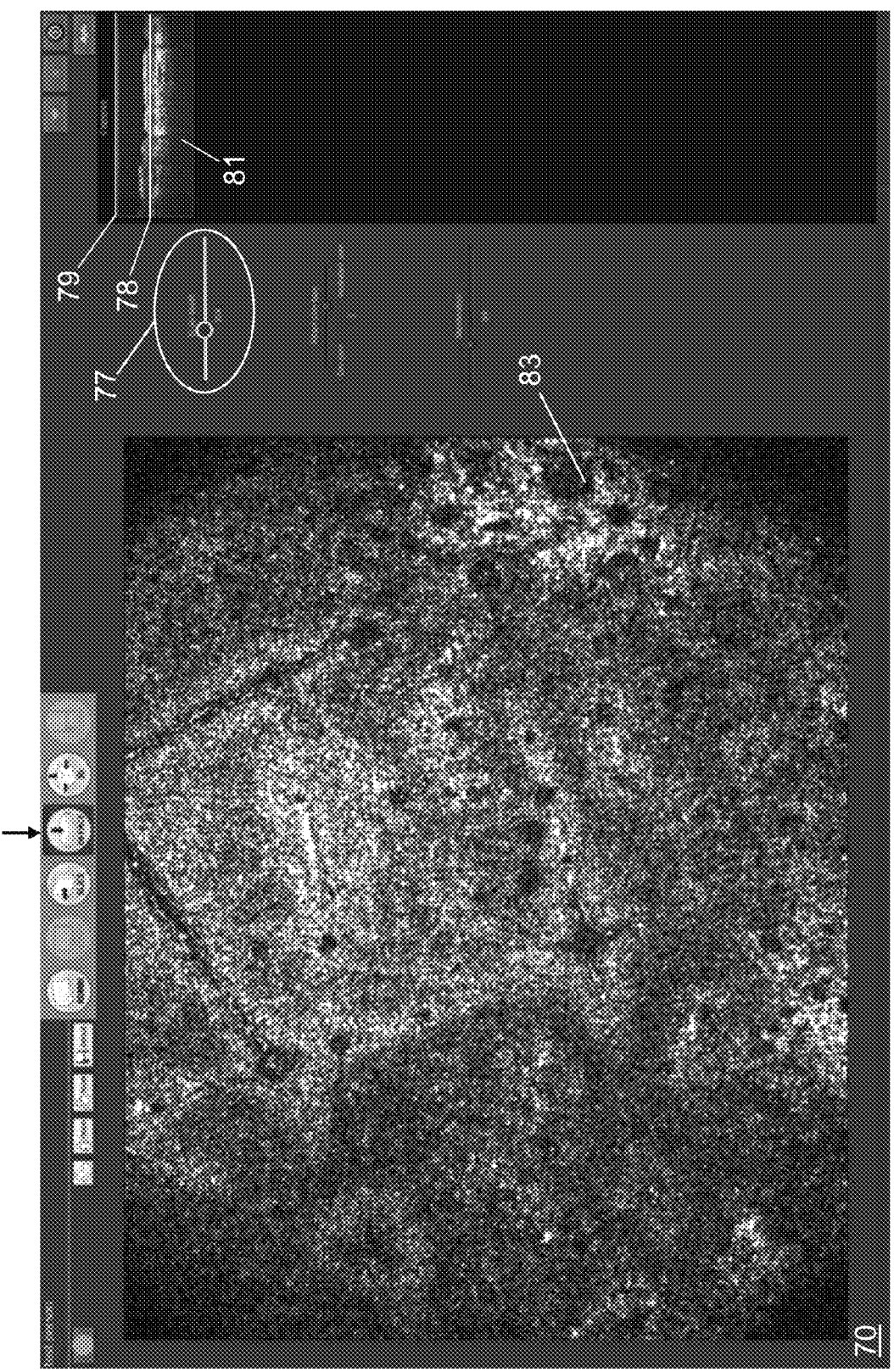
Figure 23:
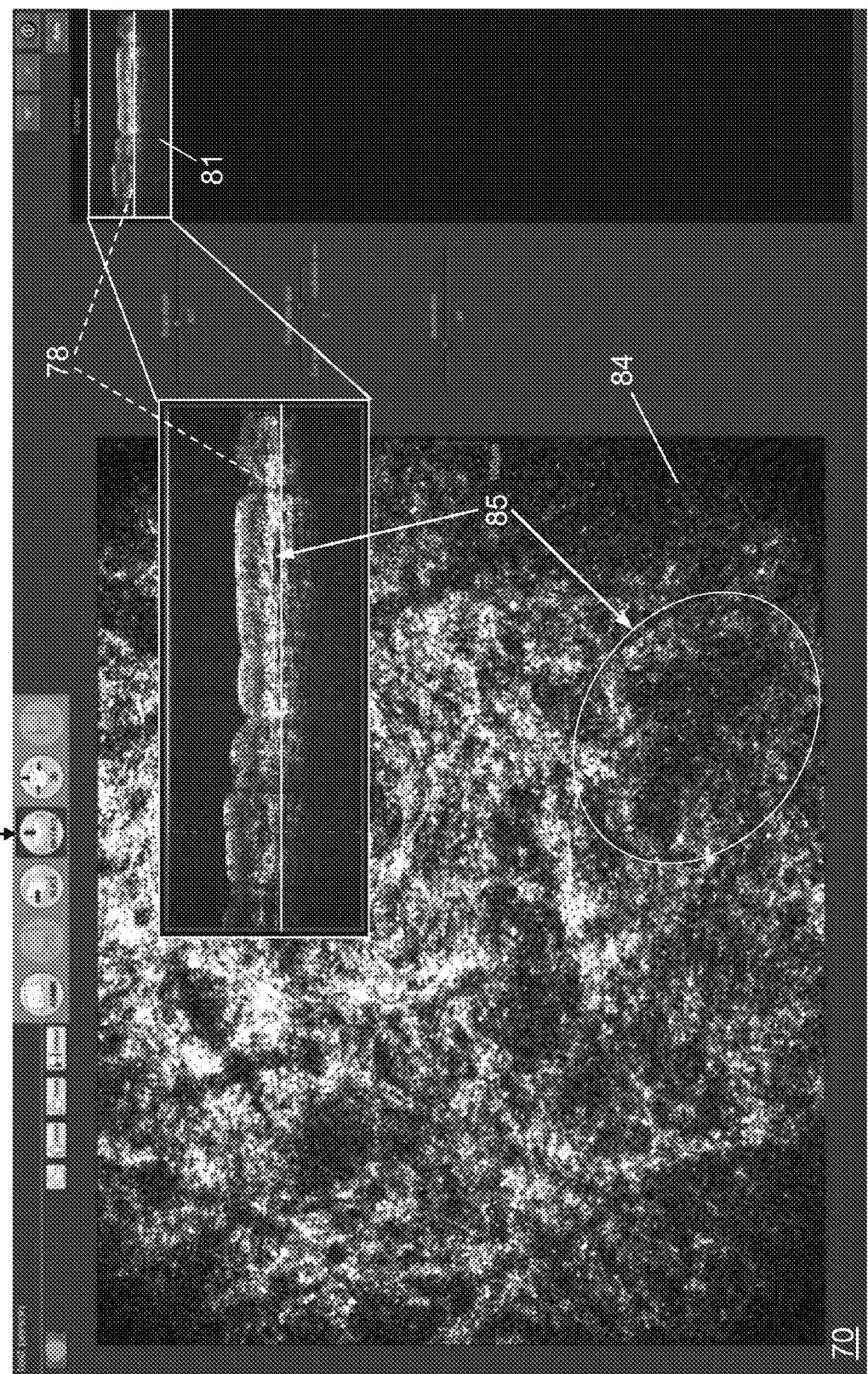
Figure 24:
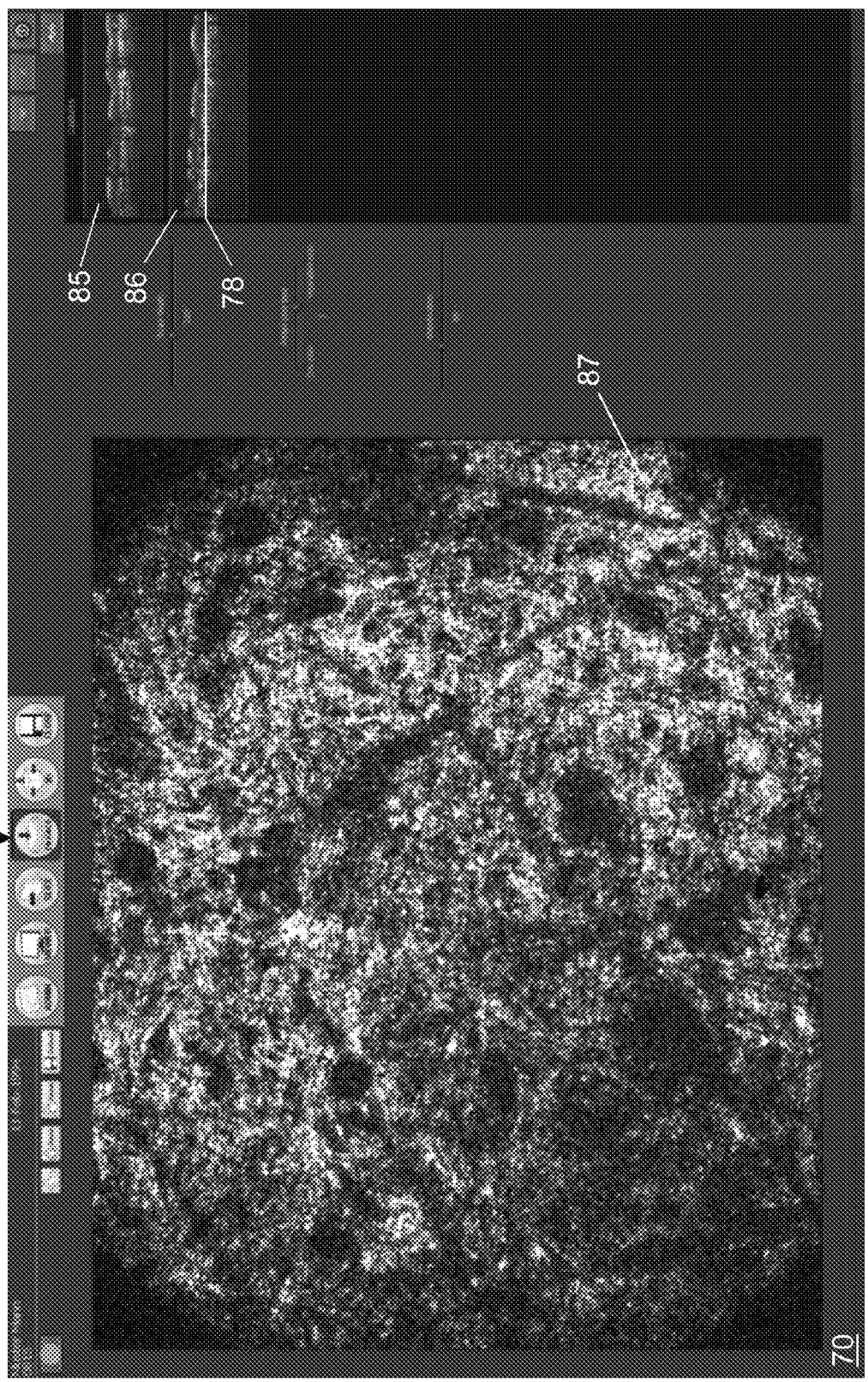
Figure 25:
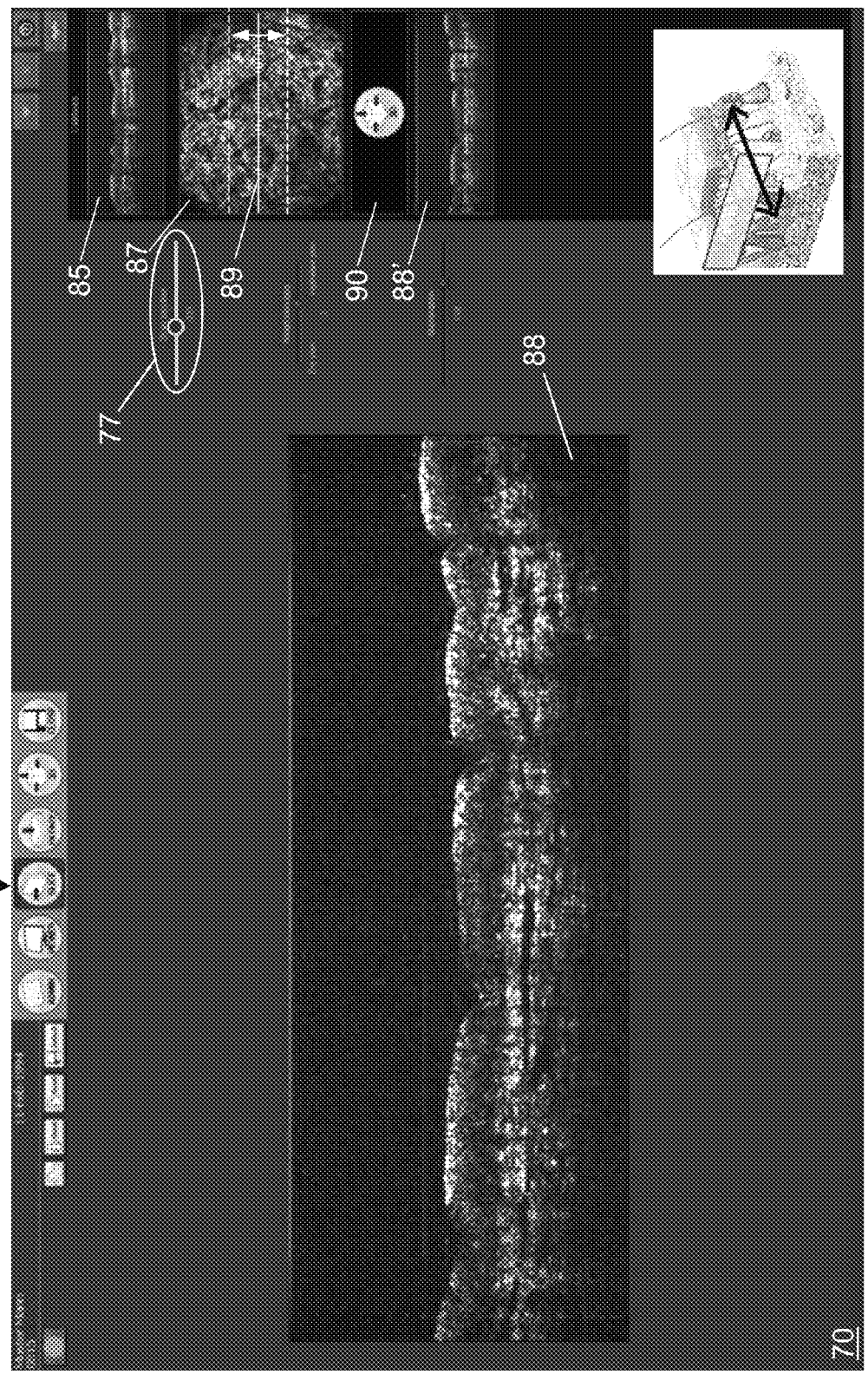
Figure 26:
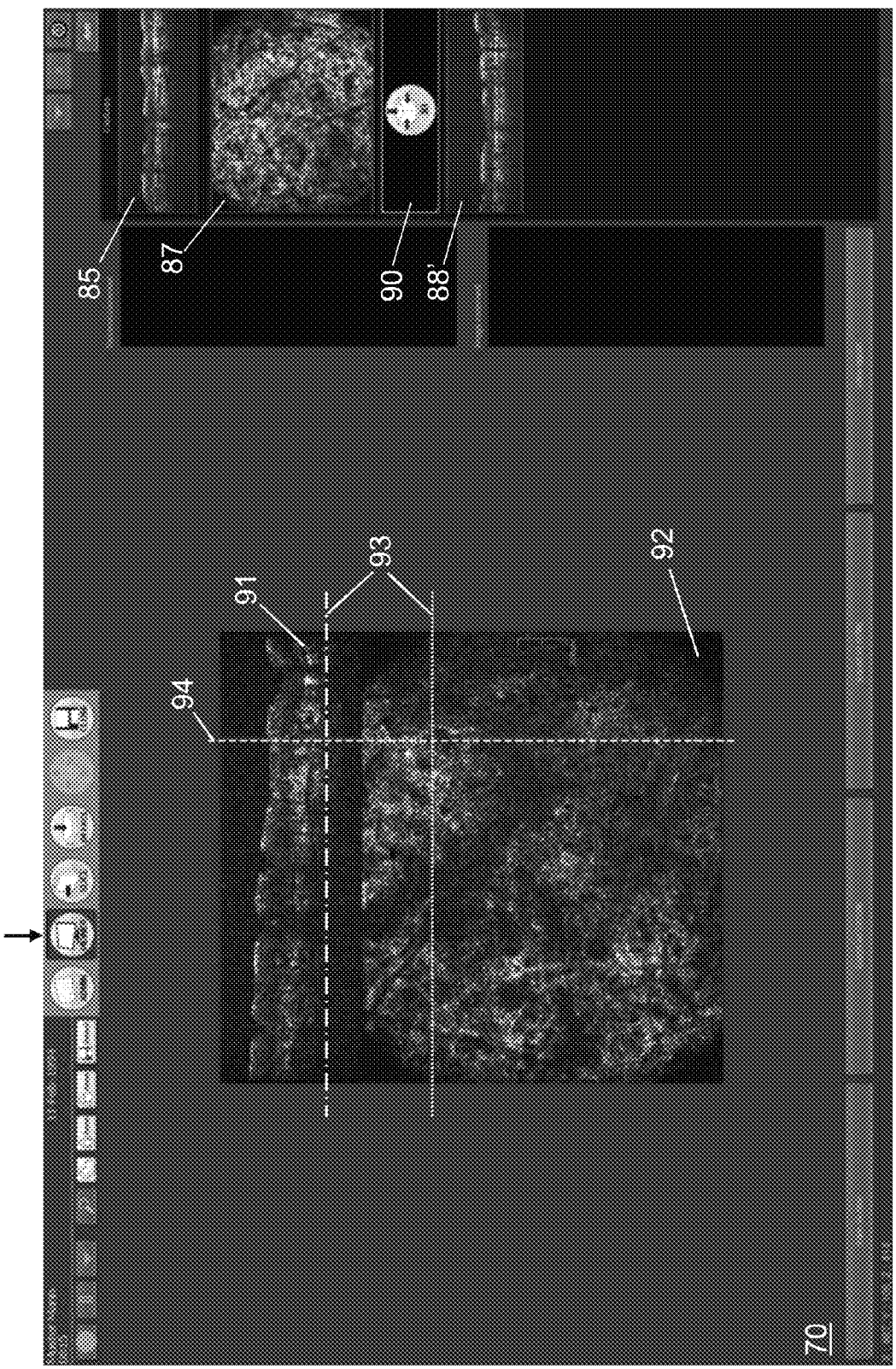
Figure 27:
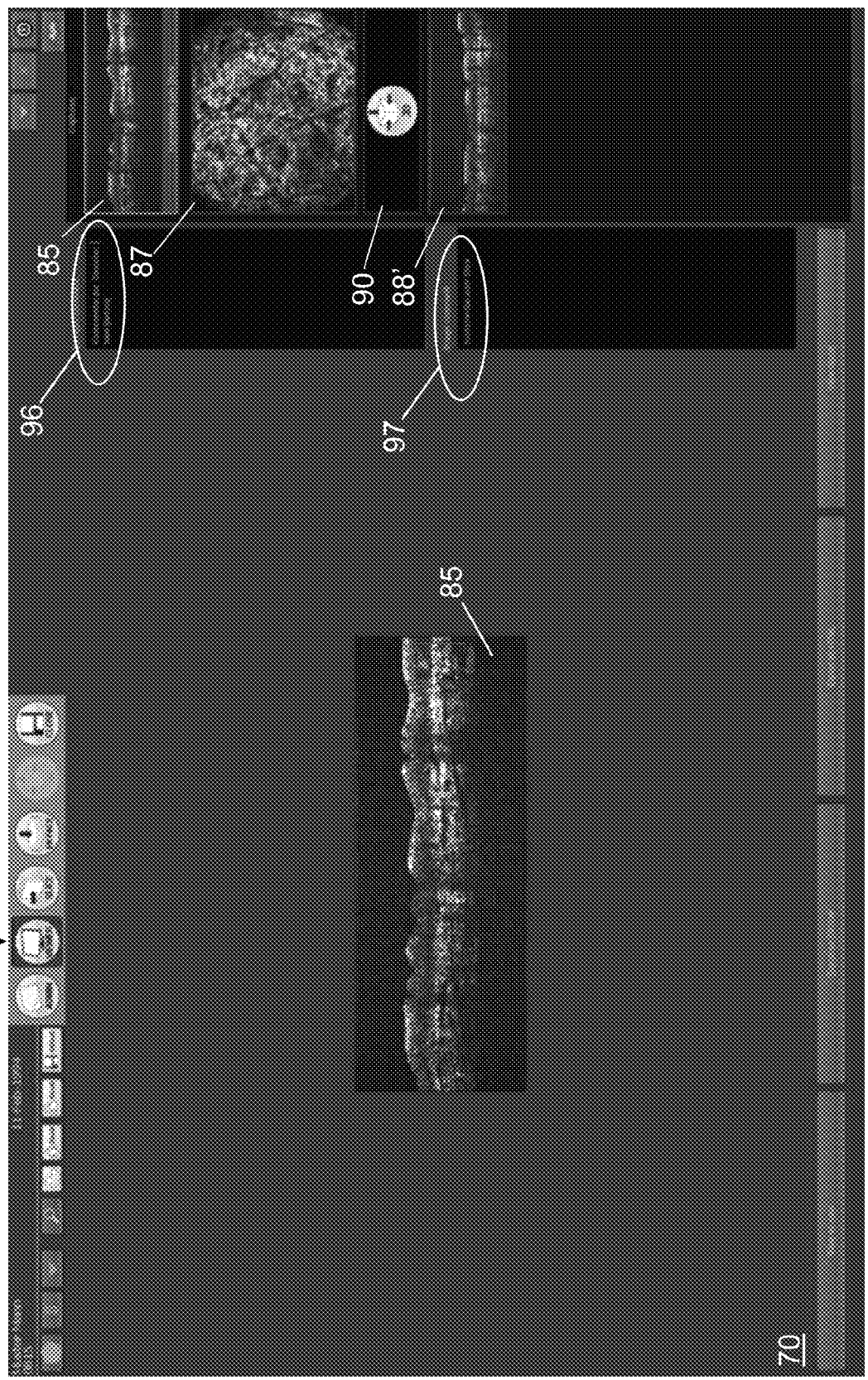
Figure 28:
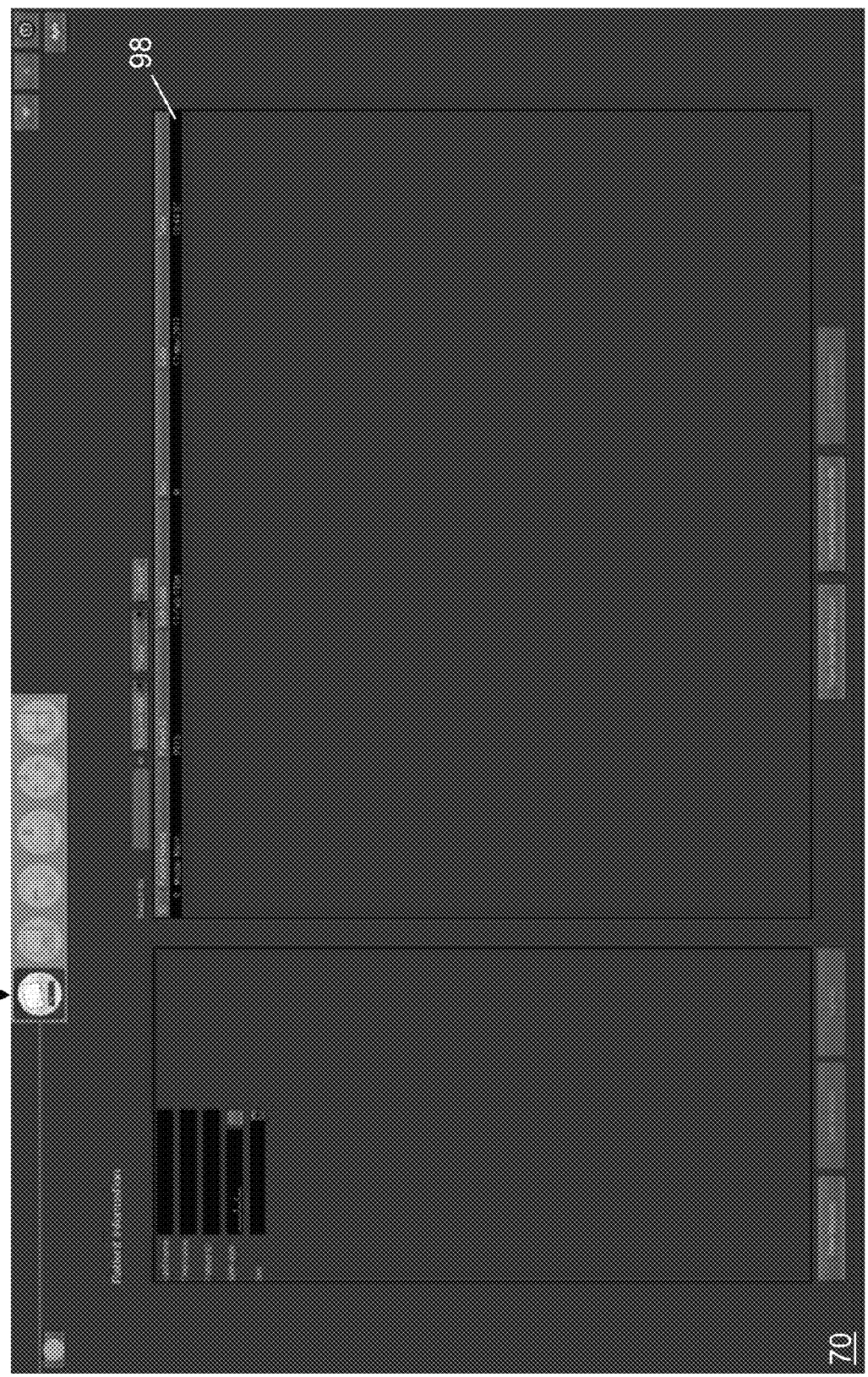
Figure 29:
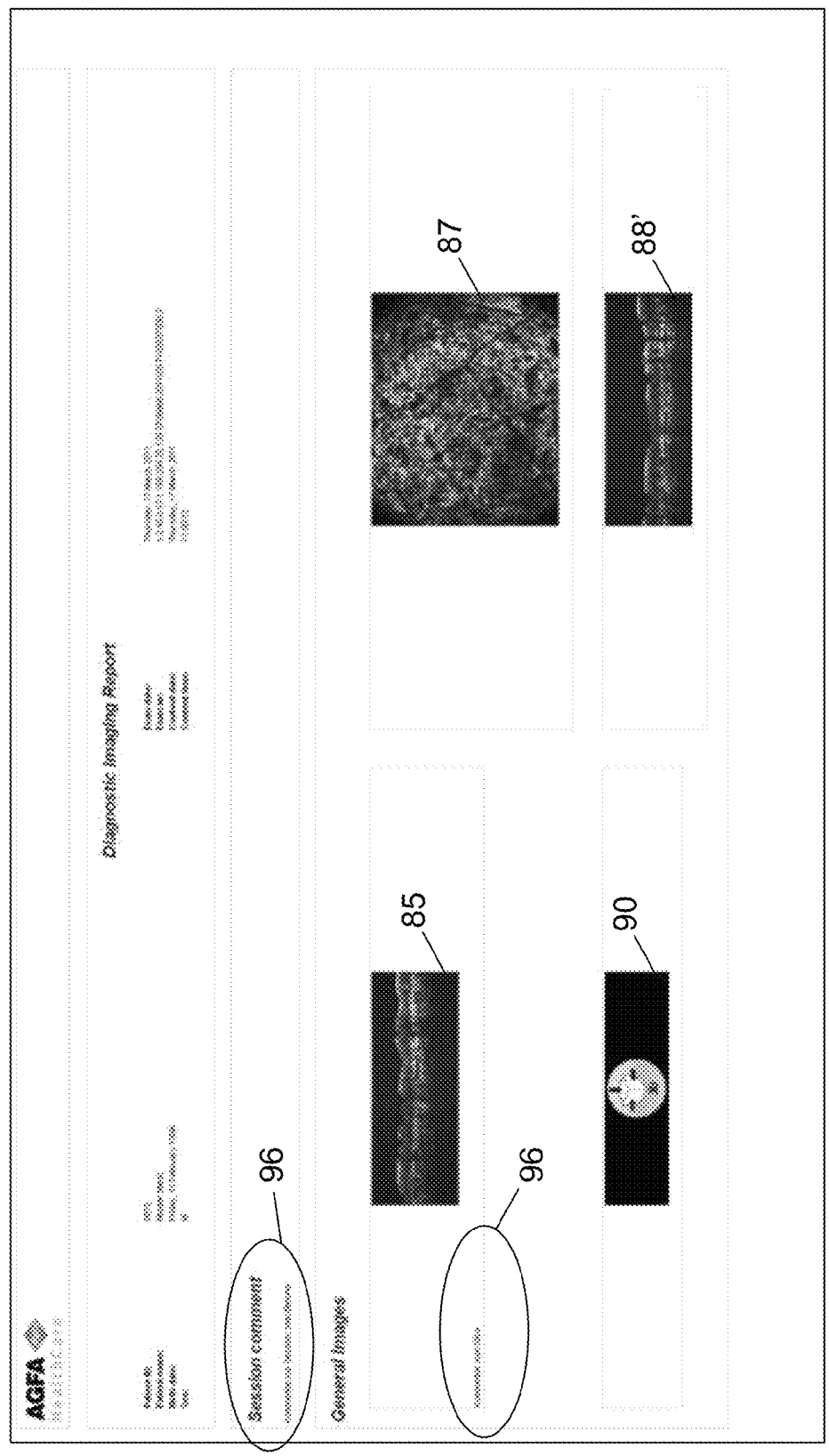

FIG. 12 an example of an initial image (left) in comparison with a corresponding final image (right) that was obtained by means of the described interpolation;

FIG. 13 a schematic representation of a system for implementing the inventive method for optical coherence tomography;

FIG. 14 a representation of a measuring head of the system;

FIG. 15 a monitor view for the illustration of the entry of patient data;

FIG. 16 a monitor view for the illustration of the display of the entered patient data;

FIG. 17 a monitor view for the illustration of the adjustment of the skin moisture;

FIG. 18 an additional monitor view for the illustration of the adjustment of the skin moisture;

FIG. 19 a first monitor view for the illustration of the selection of a second plane on the basis of a slice image;

FIG. 20 a second monitor view for the illustration of the selection of the second plane on the basis of the slice image;

FIG. 21 a third monitor view for the illustration of the selection of the second plane on the basis of the slice image;

FIG. 22 a fourth monitor view for the illustration of the selection of the second plane on the basis of the slice image;

FIG. 23 a fifth monitor view for the illustration of the selection of the second plane on the basis of the slice image;

FIG. 24 a sixth monitor view for the illustration of the display of a slice image stored in response to a user command, as well as the selection of the second plane on the basis of a temporarily stored slice image;

FIG. 25 a monitor view for the illustration of the selection of a first plane for a slice image to be acquired on the basis of an en-face image;

FIG. 26 a monitor view for the illustration of the selection of slice as well as en-face images that originate from a three-dimensional tomogram, in an image viewing mode;

FIG. 27 a monitor view for the illustration of an entry of comments in the image viewing mode;

FIG. 28 a monitor view for the illustration of an administration mode of the system; and FIG. 29 an example of an automatically generated examination report.

1. Optical Coherence Tomography Equipment

FIG. 1 shows a schematic representation of an example of an optical coherence tomography equipment, hereinafter also referred to as OCT equipment, with an interferometer 10, which comprises a beam splitter 11, an illumination arm 12, a reference arm 13, a sample arm 14, and a detector arm 15. In addition, a radiation source 21 is provided for generating light, which is filtered by an optical filter 22 and is focused through optics composed of lenses 23 and 24 onto an input region 25 of an optical waveguide 26. The radiation source 21, together with the optical filter 22, forms a device which is also designated as light source 20.

The light injected into the optical waveguide 26 is injected into the illumination arm 12 of the interferometer 10 by means of optics 28 located in the output region 27 thereof. From there, the injected light first reaches the beam splitter 11, through which it is forwarded into the reference arm 13 and reflected by a movable reference mirror 16 located at the end thereof and, after passing through the sample arm 14, illuminates an area 2 of a sample 1.

The light reflected, in particular backscattered, from the sample 1 passes through the sample arm 14 once more, is superimposed in the beam splitter 11 with the light from the reference arm 13 reflected at the reference mirror 16, and finally arrives via the detector arm 15 at a detector 30, which comprises a plurality of detector elements arranged in a, preferably flat, surface and as a consequence, facilitates a spatially resolved detection of the light reflected from the sample 30 or of a corresponding interference pattern due to the superposition thereof with the light reflected at the reference mirror 16.

A CMOS camera is preferably used as the detector 30, the detector elements (so-called pixels) of which are sensitive in the infrared spectral range, in particular in a spectral range between approximately 1250 nm and 1350 nm. Preferably, the CMOS-camera has 512×640 detector elements.

As the waveguide 26 a so-called multimode fibre is preferably used, the numerical aperture and core diameter of which, for a specific wavelength of the light injected into the fibre, allow not just one fibre mode to be formed but many different fibre modes to be excited. Preferably, the diameter of the multimode fibre used is between approximately 1 mm and 3 mm, and in particular approximately 1.5 mm.

The size of the illuminated area 2 on the sample 1 corresponds approximately to the size of the illuminated area 17 on the reference mirror 16 and is defined firstly by the optics situated at the input region of the optical waveguide 26, which in the example shown comprises the lenses 23 and 24, and secondly by the optics 28 arranged in the output region of the optical waveguide 26.

In the described OCT equipment, the resulting interference pattern is detected with the detector 30, wherein a corresponding interference signal is generated. The sampling rate of the detector 30 for sampling the interference signal must be selected such that the temporal variation of the interference pattern can be detected with sufficient accuracy. In general this requires high sampling rates, if high speeds are to be achieved for a depth scan.

A depth scan is preferably realized in the system described by causing the optical distance from the reference mirror 16 to the beam splitter 11 to be changed with a speed v during the detection of the light reflected from the sample 1 with the detector 30, by an optical path length which is substantially larger than the mean wavelength of the light injected into the interferometer 10. Preferably, the light reflected in at least 100 different depths of the sample 1 is thereby captured by the detector 30. In particular, it is preferred that the optical path is changed periodically with an amplitude which is substantially larger than the mean wavelength of the light injected into the interferometer 10. The change of the optical distance of the reference mirror 16 by the optical path or the amplitude respectively, is preferably at least 100 times, in particular at least 1000 times, greater than the mean wavelength of the light injected into the interferometer 10. Because of the large path lengths in this distance variation, this movement of the reference mirror 16 is also referred to as macroscopic movement.

Since the individual periods of an interference pattern in general need to be sampled at multiple time points respectively, the maximum possible scanning speed in the direction of the depth of the sample 1 is dependent on the maximum possible sampling rate of the detector 30. When using fast detector arrays with high spatial resolution, i.e. a large number of detector elements per unit length, the maximum sampling rate is typically in the range of approximately 1 kHz. For a mean wavelength of the light injected into the interferometer of, for example, 1300 nm, this will result in a maximum speed for the depth scan of approximately 0.1 mm/s, if four points per period of an interference structure are sampled.

To increase the speed of the depth scan, in the present OCT equipment the temporal profile of the sensitivity of the detector 30 for the light to be detected is modulated with a frequency that is up to 40% greater than or less than the Doppler frequency $f_D$, wherein the Doppler frequency $f_D$ is related to the mean wavelength $\lambda_0$ of the light injected into the interferometer 10 and the speed v of the moving reference mirror 16 as follows: $f_D=2v/\lambda_0$. Typical frequencies of this modulation are in the range between 1 kHz and 25 kHz. It is particularly preferred that the frequency of the modulation of the detector sensitivity is not equal to the Doppler frequency $f_D$.

The light reflected by the sample 1 and impinging on the detector 30 is superimposed with the modulated sensitivity of the detector 30, so that during the detection of the interference pattern impinging on the detector 30, instead of a high-frequency interference signal with a plurality of periods, the detector 30 generates a low-frequency beat signal which has markedly fewer periods than the high-frequency interference signal. In sampling this beating, considerably fewer sampling time points per time unit are therefore necessary, without losing any relevant information, than for sampling of the high-frequency interference signal without the modulation of the sensitivity of the detector 30. For a given maximum sampling rate of the detector 30, this means that the maximum speed for a depth scan of the system can be increased many times.

The sensitivity of the detector 30 can be modulated, e.g. directly or with a controllable electronic shutter arranged in front of the detector 30. As an alternative or in addition, properties of an optical element in front of the detector 30, such as e.g. the transmittance of a detector lens for the light reflected from the sample 1, can be modulated. Compared to systems with a constant detector sensitivity this increases the scanning speed by a factor of 4 or even 8.

The speed of the movement of the reference mirror 16 is in a fixed relationship to the frequency of the modulation of the sensitivity of the detector 30 and is in particular chosen such that an integral number of sampling time points, preferably four sampling time points, fit into one period of the resulting beating signal.

The beating signals sampled in this way need to be further processed prior to being displayed, since these signals still contain the interference information. The essential information to be displayed is the amplitude and depth position of the respective interference, but not the interference structure itself. In order to do this the beating signal must be demodulated, by determining the so-called envelope of the beating signal e.g. by Fourier or Hilpert transformation.

Since the phase of the beating signal is in general unknown, and this can also differ for different beating signals from different depths, a digital demodulation algorithm is used, which is independent of the phase. For sampling the interference signal with four sampling time points per period, the so-called 90° phase shift algorithms are preferably used. This allows a fast demodulation of the beating signal.

Preferably, one period of the modulation of the sensitivity of the detector 30 comprises two sub-periods, wherein during a first sub-period the detector is sensitive and during a second sub-period the detector is insensitive to the light to be detected. In general, the first and the second sub-period are equal in length. However, it can be advantageous to choose a different duration for the first and second sub-period. This is the case, for example, when the intensity of the light emitted by the light source 20, or injected into the interferometer 10, and/or of the light reflected from the sample 1, is relatively low. In these cases the first sub-period can be selected such that its duration is longer than the duration of the second sub-period. In this way, even at low light intensities, in addition to a high depth scanning speed, a high signal-to-noise ratio, and thus a high image quality, is ensured.

Alternatively to the sensitivity of the detector 30, the intensity of the light injected into the interferometer 10 can also be temporally modulated, wherein the remarks on the modulation of the detector sensitivity described above, apply accordingly with regard to the preferred embodiments and the advantageous effects.

The radiation source 21 preferably includes a spiral-shaped wire, which is surrounded by a transparent casing, preferably made of glass. Preferably, the radiation source 21 is implemented as a halogen light bulb, in particular a tungsten halogen bulb, where a tungsten filament is used as wire and the inside of the casing is filled with gas, which contains a halogen, e.g. iodine or bromine. By application of an electrical voltage, the spiral wire is made to glow, which causes it to emit spatially incoherent light. The term spatially incoherent light within the context of the present invention is to be understood as light whose spatial coherence length is less than 15 µm, and in particular only a few µm, i.e. between approximately 1 µm and 5 µm.

The spatially incoherent light generated by the radiation source 21 passes through the optical filter 22, which is implemented as a band-pass filter and essentially only transmits light within a specifiable spectral bandwidth. The optical filter 22 has a bell-shaped or Gaussian spectral filter characteristic, wherein only those spectral light components of the light generated by the radiation source 21 which lie within the specified bandwidth about a mean wavelength of the bell-shaped or Gaussian spectral filter characteristic can pass through the optical filter 22.

A Gaussian spectral filter characteristic within the context of the invention is to be understood to mean that the transmittance of the optical filter 22 for light with particular wavelengths $\lambda$ is proportional to $\exp[-[(\lambda-\lambda_0)/2\cdot\Delta\lambda]^2]$, where $\lambda_0$ designates the wavelength at which the optical filter 22 has its maximum transmittance, and $\Delta\lambda$ the standard deviation, which is related to the full width at half maximum (FWHM) of the Gaussian transmittance curve as follows: FWHM≈2.35·$\Delta\lambda$.

A bell-shaped spectral filter characteristic is to be understood as a spectral plot of the transmittance of the optical filter, which can be approximated by a Gaussian function and/or only deviates from a Gaussian function to the extent that its Fourier transform has essentially a Gaussian shape with either no secondary maxima or only a small number of very low secondary maxima, the height of which is a maximum of 5% of the maximum of the Fourier transform.

The use of a radiation source 21 which a priori generates spatially incoherent light, in the detection of the light reflected by the sample 1 by means of the two-dimensional spatially resolving detector 30, prevents the occurrence of so-called ghost images caused by coherent crosstalk between light beams from different locations within the sample 1 under test. The additional equipment for destroying the spatial coherence, which is normally required when using spatially coherent radiation sources, can thereby be omitted.

In addition, thermal radiation sources such as e.g. incandescent or halogen lamps can therefore be used to produce incoherent light, which are much more powerful and more cost-effective than the frequently used superluminescent diodes (SLDs).

Due to the optical filtering with a Gaussian or bell-shaped filter characteristic, the light generated by the radiation source 21 is converted into temporally partially coherent light with a temporal coherence length of preferably more than approximately 6 μm. This is particularly advantageous with the described OCT equipment which is of the so-called time-domain OCT type, in which the length of a reference arm 13 in the interferometer 10 changes and the intensity of the resulting interference is continuously detected by means of a preferably two-dimensional detector 30 because, by filtering the light using the bandpass realized by the optical filter 22 on the one hand, a high lateral resolution of the image captured from the sample 1 is obtained, and on the other hand, due to the Gaussian or bell-shaped spectral filter characteristic of the optical filter 22, the occurrence of interfering secondary maxima in the Fourier transform of the interference pattern detected by the detector, which would cause the occurrence of further ghost images, is avoided.

Overall, the described OCT equipment allows obtaining OCT images with high resolution and image quality in an easy way.

In the example shown, the optical filter 22 is arranged between the radiation source 21 and the optics formed from the two lenses 23 and 24 on the input side. In principle, it is also possible however to provide the optical filter 22 between the two lenses 23 and 24 or between the lens 24 and the input region 25 of the optical waveguide 26. Essentially, an arrangement of the optical filter 22 is particularly advantageous if the light rays impinging on the optical filter 22 have only a small divergence, or in particular run parallel to one another, because, firstly, this reduces reflection losses at the boundary surfaces of the optical filter 22 and secondly, it prevents any beam displacement due to light refraction. In the example shown therefore, an arrangement of the optical filter 22 between the two lenses 23 and 24 of the optics is preferred.

Alternatively or in addition, it is also possible however to mount the optical filter 22 directly on the casing of the radiation source 21. This has the advantage that an additional filter component can be dispensed with.

Alternatively or in addition, it is also possible however to arrange the optical filter 22 between the output region 27 of the optical waveguide 26 and the illumination arm 12, for example in front of or between the lenses of the optics 28 located between the output region 27 of the optical waveguide 26 and the input of the illumination arm 12.

In a simple and highly reliable variant the optical filter 22 comprises an absorption filter, in particular a so-called dyed-in-the-mass glass, and an interference filter, wherein multiple, preferably between about 30 and 70, thin layers with different refractive indices are applied to the dyed-in-the-mass glass, for example, by vapour deposition, which results in an interference filter.

For the case where the optical filter 22 is integrated into the casing of the radiation source 21, the optical filter 22 is preferably implemented by applying such interference layers to the casing. As an alternative, or in addition, it is also possible however to provide one or more of the lenses 23, 24 or the lenses of the optics 28 with a corresponding interference filter.

2. Operating Modes of the OCT Equipment

The described OCT equipment can be operated in three different operating modes. The operating modes entail two real time modes, where OCT images of sample 1 are generated at a high rate of at least one image per second, preferably approximately 5 to 10 images per second, as well as one static operating mode.

In the first operating mode, real time mode 1, two-dimensional depth sections of sample 1 are generated (so-called slices). This is realized by using a CMOS camera as the detector 30, which permits the adjustment of a so-called window of interest (WOI), where only a partial surface of the detector 30 is sensitive to light and converts the same to corresponding detector signals. The reduction of the sensitive camera surface is associated with a distinct increase in camera speed, so that with this setting more camera images can be generated per second than in the full-image mode.

In the real time mode 1 a WOI is preferably selected that matches the entire camera length or width (for example 640 pixels) along one direction, and has the—determined by the type of respective camera—least possible number of pixels (for example 4 pixels) in the other direction. As a result the speed of the camera is increased to such an extent that OCT images can be acquired in real time.

This is preferably achieved with the previously described modulation of the sensitivity of the detector 30 or the modulation of the intensity of the light injected into the interferometer 10, or the light emitted by the interferometer 10.

By way of example, FIG. 2 shows a detector 30 with a detector surface A1, which comprises a first plurality N1 of detector elements 31 arranged in a plane, and has a length c1 and a width b1. With the setting of a WOI as stated above, light is only detected by the detector elements 31 that are located in a partial surface A2 of the detector surface A1, and converted into corresponding detector signals. The second plurality N2 of the detector elements 31 of the partial surface A2 is smaller than the first plurality N1 of the detector elements 31 of the entire detector surface A1. The lengths c1 and c2 of the detector surface A1 or partial surface A2 are equal in size, while the widths b1 and b2 of the detector surface A1 or partial surface A2 differ.

In the shown example the partial surface A2 is only 4 pixels wide, while the detector surface A1 is 512 pixels wide. The sensitive surface of the detector surface A1 is consequently reduced by a factor of 128, which significantly shortens the time duration required for the detection of the interference patterns and their conversion to corresponding detector signals.

As displayed in FIG. 3, only four (corresponding to the four pixel rows of the partial surface A2) two-dimensional depth sections S (so-called slices) are obtained in this example from the observed spatial element R of sample 1, instead of a full three-dimensional tomogram. Due to the slices that are obtained in the first operating mode, this mode is also referred to as the slice mode.

For purposes of further illustration the left part of FIG. 3 shows a model of the human skin, where as an example a plane of a two-dimensional depth section or slice acquired in operating mode 1, preferably in real time, is delineated.

In the second operating mode, the real time mode 2, two-dimensional tomograms F are generated—as displayed in FIG. 4—at a certain depth T of the observed spatial element R of sample 1, wherein the depth T can be arbitrarily selected. Hereby the entire detector surface A1 of the detector 30 is used for the detection of the light reflected by sample 1 and the conversion thereof into corresponding detector signals, wherein however only maximally five camera images in each case are considered for the calculation of a tomogram F. To that end the reference mirror 16 is moved periodically in the interferometer 10 at a certain distance to the beam splitter 11 at an amplitude of about 1 μm about this distance, while up to five camera images are acquired, which are then computed into an OCT image. In this manner tomograms F can be generated at a high repetition rate, in particular in real time. In comparison to the macroscopic movement of the reference mirror 16 described above the movement of the reference mirror 16 in this case is microscopic.

The depth T at which the tomogram F is obtained can be arbitrarily selected by means of the macroscopic movement of the reference mirror 16—if applicable in combination with focus tracking, which is described in more detail further below, of the light that is focused at a certain depth T in the sample by means of the sample optics that are located in the sample arm 14.

On the basis of the two-dimensional cuts F obtained in the second operating mode, through the sample 1 in planes that run substantially perpendicular to the direction of the light impinging on the sample 1, the second operating mode is also referred to as en-face mode.

For purposes of further illustration the left part of FIG. 4 shows a model of the human skin, where as an example a plane of a two-dimensional tomogram or en-face image acquired in operating mode 2, preferably in real time, is delineated.

In a third operating mode, a static mode, a complete three-dimensional data set is acquired with the aid of the macroscopic movement of the reference mirror 16 in combination with focus tracking.

At a mean wavelength of the light that is injected into the interferometer 10 in the range of, for example, 1 μm the optical path length or amplitude of the macroscopic movement of the reference mirror 16 is at least approximately 0.1 mm, preferably at least approximately 1 mm.

In contrast to the conventional microscopic amplitude of the reference mirror movement, which is on the order of magnitude of the mean wavelength of the injected light, i.e. of up to typically 1 μm, in the described OCT equipment a macroscopic movement of the reference mirror 16 on the order of magnitude of 0.1 mm up to several millimeters takes place.

During the macroscopic linear movement of the reference mirror 16, the light reflected by sample 1 is forwarded to the two-dimensional detector 30 via the interferometer 10 and detected by said detector successively at several time points for a certain time duration, which corresponds to the integration time of the detector 30, in each case, and converted into corresponding detector signals.

In order for the light reflected from the reference mirror 16 and from the sample 1 to be able to interfere, the so-called coherence condition has to be satisfied, which states inter alia that the respectively reflected light waves must have a constant phase relation relative to one another in order to be able to interfere with one another. Due to the use of light with a very short coherence length of typically 10 μm or less, the condition of a constant phase relation is only satisfied at certain depths or depth ranges of the sample 1, which is also referred to as coherence gate.

Each position of the reference mirror 16 during the macroscopic movement corresponds thereby to a certain depth within the sample 1, or to a depth range about this certain depth for which the coherence condition is satisfied, so that the light reflected by the reference mirror 16 and by the sample 1 can interfere.

In the case of a periodic movement of the reference mirror 16, both half-periods of the periodic movement of the reference mirror 16 can each be used for the acquisition of detector signals.

In this manner successive two-dimensional cuts are acquired by the detector 30 at different depths of the sample 1. This is illustrated in FIG. 5, where—representative for a plurality of two-dimensional cuts—a first, second and third two-dimensional cut F1, F2 and F3 respectively through a spatial element R is displayed. Such a two-dimensional cut "propagates" synchronously with the macroscopic movement of the reference mirror 16 in direction "a" through the observed spatial element R of the sample 1, without the same having to be moved.

Every cut F1, F2 and F3 is located at a depth T1, T2 and T3 respectively of the sample 1, at which depth the coherence condition is satisfied in each case, so that the light reflected by the reference mirror 16 and by the sample 1 can interfere. The macroscopic movement of the reference mirror 16 in combination with the successive two-dimensional detection of the light reflected by the sample 1 therefore has the effect of a three-dimensional depth scan.

The combination, as described above, of the macroscopic linear movement of the reference mirror 16 on the one hand with the detection of the light reflected by the sample 1 with a two-dimensional detector 30 on the other, facilitates a straightforwardly implemented and quick acquisition of a complete three-dimensional data set of the desired spatial element R1 of the sample 1.

Due to the macroscopic movement of the reference mirror 16 a three-dimensional tomogram is hereby obtained instead of just a two-dimensional image at a certain depth. In the process the sample 1 has to be no longer moved relative to the second interferometer 20 for the acquisition of a three-dimensional data record. This makes the described OCT equipment compact, reliable and straightforwardly handleable, so that the same is particularly suitable for in vivo use.

The left part of FIG. 5 shows, for further illustration, a model of the human skin, where as an example a spatial element is delineated, of which in operating mode 3 a three-dimensional tomogram is acquired.

3. Focus Tracking

The OCT equipment described above is designed such that during a full stroke, meaning the path length or twice the amplitude, of the movement of the reference mirror 16 an interference signal of sufficiently high intensity and high sharpness is always obtained. As a result of the focus tracking, which is described hereinafter, assurance is furthermore provided that the interference signal as well as the sharpness of the detected interference pattern are maximized for all depths in the sample 1.

To that end, during the detection of the light that is reflected from the sample 1, the focus, meaning the focal point of the imaging optics of the interferometer 10 that is located in the sample arm 14, is adjusted in such a manner that the location of the focus in the sample 1 and the location of that plane in the sample 1 for which in case of a reflection of light the coherence condition is satisfied and interference occurs, are essentially identical at all times during the acquisition of a tomogram of the spatial element R of the sample 1. This is illustrated in what follows on the basis of FIGS. 6a and 6b.

Figure 6A:
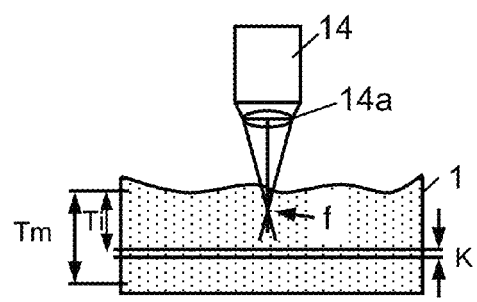

FIG. 6a shows the case where the focus f of the—here only shown simplified as a lens—sample objective 14a in the sample arm 14 is located at a depth of the sample 1 that does not coincide with the location of the coherence gate K. As a result the cut, through sample 1, that was obtained within the coherence gate K at a depth Ti is not imaged exactly in focus onto the detector 30 (see FIG. 1), so that information losses would have to be accepted while detecting the interference.

Figure 6B:
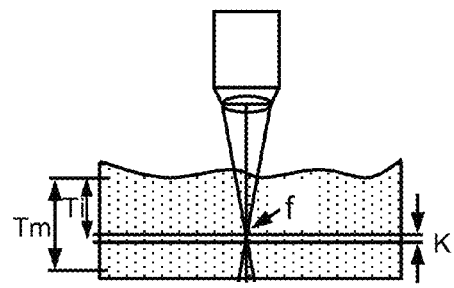

In FIG. 6b, on the other hand, the case is displayed where the focus f of the sample objective 14a is set such that it is located within the coherence gate K at a depth Ti. This tracking of the focus f of the sample objective 14a, corresponding to the depth Ti of the coherence gate K in each case, is referred to as focus tracking. In this manner the interferometer 10 is focused during the depth scan on the respective location of the coherence gate K at different depths Ti of the sample 1, so that images with a high sharpness are obtained from any depth of sample 1.

The maximum optical scan depth Tm specifies to what depth beneath the surface of the sample 1 the coherence condition for constructive interference is satisfied, and corresponding interference patterns are obtained.

The sample objective 14a, which is displayed in FIGS. 6a and 6b in a simplified manner, preferably comprises several lenses that can be moved, individually and/or in groups, in the direction toward the sample 1 or away from the same. To that effect a piezo-electric actuator, for example, is provided, in particular an ultrasound piezo motor, which is coupled with the sample objective 14a or the lenses, and moves the same along one or several guideways, in particular guide rods or guide grooves.

The movement of the sample objective 14a or the lenses takes place preferably synchronously with the macroscopic movement of the reference mirror 16 in the interferometer 10 (see FIG. 1). In this manner the focus f of the sample objective 14a tracks the coherence gate G, while the latter traverses successively different depths T1, T2 and T3 of the sample 1, from which two-dimensional cuts F1, F2 and F3 (see FIG. 5) are acquired respectively with the aid of the detector 30.

The synchronization of the macroscopic movement of the reference mirror 16 and the focus tracking on the one hand, in combination with a two-dimensional detector 30 on the other, assures a particularly straightforward and quick acquisition of a plurality of in-focus two-dimensional image sections at different depths of the sample 1, and thereby the acquisition of a full three-dimensional image data set of high image quality.

Since the interferometer 10 and the optical imaging in the sample arm 14 are continuously matched to one another, the interference signals detected by the detector 30 are at a maximum for any depth in the sample 1, so that a very high signal to noise ratio results. Assurance is thereby furthermore provided that the lateral resolution is optimal for all depths in the sample 1, because the focus f of the imaging is always located within the coherence gate K. As a result OCT images with a faithful detail rendering and a high contrast are obtained.

Advantageously the speed v2 of the movement of the lens or the lenses of the sample objective 14a in the direction of the sample 1 is smaller than the speed v1 of the movement of the reference mirror 16. Preferably a ratio v1/v2 of the speeds of the reference mirror 16 and the lenses is hereby selected, which is approximately equal to $2 \cdot n - 1$, or is up to about ±20%, preferably up to about ±10%, around this value. The location of the focus f and coherence gate G is hereby matched to one another with particularly high reliability.

As a result of the previously described selection of the ratio v1/v2 of the speeds of the reference mirror 12 and the lenses 42, assurance is provided that the coherence gate K and focus f are superimposed on one another during the depth scan over the entire depth range being observed. In the example above of a sample with an index of refraction of n=1.4, the ratio v1/v2 of the speeds is in the range of approximately $(2 \cdot 1.4 - 1) \pm 20\%$, meaning between approximately 1.44 and 2.16, and is preferably approximately $2 \cdot 1.4 - 1 = 1.8$.

4. Trilinear Interpolation

The OCT images obtained with the OCT equipment and method described above can undergo an interpolation for the further improvement of the identification of diagnostic information, for example in the area of dermatology for the further improved identification of cavities or bulges in the skin that have a size of larger than approximately 10 μm.

A particularly advantageous interpolation method, in the context of OCT images, particularly real time images, obtained with the OCT equipment and method described above, is the so-called trilinear interpolation, where the initial image values of at least two two-dimensional initial images, which were acquired in planes of the object running parallel to one another, are interpolated in three-dimensional space, so that a two-dimensional final image is obtained. This is explained in detail in what follows.

The trilinear interpolation relates to a method for the multi-variate interpolation in a three-dimensional regular grid, i.e. a grid with the same grid constant in all three spatial directions. This is illustrated using the grid shown in FIG. 7 as an example. On the basis of an interpolation of the initial image values located on the eight corners C000 to C111 of a cube, an interpolation value located in the center point C of the cube is derived in each case.

The respective initial image values originate from initial images acquired in different planes of the object. The initial image values are light intensity values at different locations in the corresponding two-dimensional initial images. The initial image values, i.e. the light intensity values, with the coordinates C000, C001, C011 and C010 originate, for example, from a first real time image acquired in the operating mode 1 along a first depth section S (see FIG. 3), and the initial image values, i.e. the light intensity values, with the coordinates C100, C101, C111 and C110, originate from a second real time image acquired in the operating mode 1 along a second depth section S (see FIG. 3), spaced apart therefrom at a distance of the grid constant. The initial image values with the coordinates C000, C010, C110 and C100 originate, in an alternative example, from a first real time image acquired in the operating mode 2 in the form of a first two-dimensional tomogram F (see FIG. 4), and the initial image values with the coordinates C001, C011, C111 and C101 originate from a second real time image acquired in the operating mode 2 in the form of a second two-dimensional tomogram F (see FIG. 4), spaced apart therefrom at a distance of the grid constant.

An identical resolution in all three spatial dimensions is selected for a trilinear interpolation of the OCT images, in particular the real time images, obtained with the OCT equipment and method described above.

This cannot be achieved without loss of resolution with OCT systems known from prior art because usually only a relatively high axial (i.e. longitudinal, in the direction of the light impinging on the object) resolution can be realized, while the lateral (i.e. the transverse, perpendicular to the direction of the light impinging on the object) resolution is usually considerably lower. A selection of equal resolution in all three spatial directions would therefore only be possible by lowering the axial resolution, which as a rule however is not desirable because of the large loss of information, since small objects can in that case no longer be resolved. In addition it is not possible with OCT systems known from prior art to sample two two-dimensional images simultaneously, or at least almost simultaneously. This applies particularly to en-face images and scanning systems. A trilinear interpolation in real time is therefore almost impossible because in that case movement artifacts also become relevant.

In contrast, in the case of the OCT images obtained with the OCT equipment and method described above, a trilinear interpolation is possible in the case of the two-dimensional real time images captured in the operating modes 1 and 2 (slice or en-face), as well as also for the post-processing of the three-dimensional tomograms obtained in the static operating mode 3.

The axial (i.e. longitudinal) resolution is determined, in the case of the OCT equipment described above, primarily by the spectral bandwidth of the light source 20 and the index of refraction of the examined object 1, while the lateral (i.e. transverse) resolution is determined primarily by the optical imaging and the size of the detector elements 31 of the detector 30 (see FIGS. 1 and 2).

The OCT equipment described above is tuned in such a way that lateral and axial resolution are almost equal and very high. Preferably the resolution in all three dimensions is approximately 3 µm×3 µm×3 µm.

For the lateral resolution this is achieved in particular through the focus tracking described above, and for the axial resolution in particular through the use of a light source 20, which comprises a halogen lamp as a radiation source 21 in combination with a Gaussian filter 22.

Furthermore preferred is that the depth of field of the imaging optics, in particular the sample objective 14, of the interferometer 10 (see FIG. 1) is larger than the "grid spacing" of the initial image values, i.e. the spatial distance of the initial image values in the three dimensions. This provides assurance in every case that the initial image values are always captured with high accuracy.

Preferably the fact is furthermore taken into account that the sampling of the interference signal must be high enough so as not to violate the so-called sampling theorem. This is explained in detail hereinafter.

FIG. 8 shows a scheme for the illustration of the sampling of an interference pattern 40 in the direction of the depth T of an object, in comparison with the physical resolution 41 in the direction of depth T. With the OCT equipment and method described above, four points 42 each are preferably sampled per interference period of the interference pattern 40. An interference period in this case is the length of a half (mean) wavelength of the light injected into the interferometer (at a mean wavelength of approximately 1.3 µm this corresponds to approximately 0.65 µm). Consequently the distance 43 between two sampling points 42 is approximately 0.163 µm. The physical resolution 41 in air is however approximately 4 µm. This means that approximately 24 sequential lines in the depth direction T contain approximately the same physical information, and can therefore be combined into one line without significant loss of information. This in turn has the effect that the resulting volume image point (so-called voxel) has almost the same extent in all three dimensions, meaning it corresponds substantially to a cube. The initial image value corresponds thereby, for example, to a mean value or the median of the original initial image values.

FIG. 9 illustrates the previously described combining of original initial image values, which were sampled in the direction of the depth T of the object in several sequential lines 44, to one line of only one initial image value and one line height, i.e. a longitudinal extent 45 in the depth direction T that corresponds to the lateral extent 46 of an image point (pixel) of the line, perpendicular to the depth direction T.

In operating mode 1, where slices are acquired in real time, two neighboring lines of the detector 30 are simultaneously read out in the case of the trilinear interpolation. In the example of the detector 30 shown in FIG. 2 this means that the width b2 of the partial surface A2 of the detector 30 is selected such that said width extends only across two detector elements 31 in the direction of the width of the detector 30. The partial surface A2 in that case comprises only 2×640 detector elements 31 that are successively read out during a macroscopic movement of the reference mirror 16 (see FIG. 1), and are computed into a two-dimensional final image in the manner described above.

This is illustrated on the basis of FIG. 10. Two initial images S in the form of two depth sections (compare FIG. 3), which were acquired in the direction of the depth T of the object, are combined to a final image S' using trilinear interpolation.

Since the two initial images S in the form of two depth sections are acquired simultaneously and within a very short time, it is assured that a possible relative movement between sensor head and object, in particular the human or animal skin, is of no significance during the acquisition of the two two-dimensional initial images S.

In the operating mode 2, in which en-face images are acquired in real time, the reference mirror 16 (see FIG. 1), which is located in a mean position, performs only a microscopic, preferably oscillating, movement from approximately +/−5 µm to +/−40 µm. In this case the position or optical imaging property of the sample objective 14 is preferably set in such a way that a focal point thereof has a mean depth position that is predefined by the macroscopic displacement of the reference mirror 16. In the case of the trilinear interpolation of the en-face images acquired in real time—in contrast to operation without trilinear interpolation—two initial images in the form of two en-face images are captured each at two different positions of the reference mirror 16, and computed into a two-dimensional final image in the form of an en-face image.

This is illustrated on the basis of the diagram shown in FIG. 11, which shows the progression of the position P of the reference mirror 16 over time t.

In the left part of the diagram of FIG. 11 the case without trilinear interpolation is displayed. In the operating mode 2 a two-dimensional initial image F is hereby obtained in the form of a tomogram from a certain depth in the object, by measuring at five positions P of the reference mirror 16, which positions are located symmetrically about a mean position $P_0$.

In the right part of the diagram of FIG. 11 the application of the trilinear interpolation is illustrated. Two two-dimensional initial images F are obtained by measuring at five positions P of the reference mirror 16 in each case. The five positions P are located each symmetrically about the positions $P_1$ and $P_2$, which preferably are themselves located symmetrically about the mean position $P_0$ of the reference mirror 16. The distance 47 between the positions $P_1$ and $P_2$ of the reference mirror 16 is in this case determined by the axial and/or lateral pixel size 45 and 46 respectively (see FIG. 9). With the preferred symmetric location of the positions $P_1$ and $P_2$ the corresponding tomograms F each are located in the object above and below the mean depth location by half a pixel size. The initial images F acquired in this manner then undergo a trilinear interpolation, during which the final image F' is obtained.

Preferably the depth of field of the optical imaging in the interferometer 10 (see FIG. 1) is selected such that the same is larger than half the voxel size. With a preferred voxel size of 3 μm, the depth of field must therefore be larger than 1.5 μm.

Since the described acquisition of the two initial images in the operating mode 2 takes place immediately one after the other, typically temporally separated by about 0.014 seconds, the effect on the obtained final image of a possible relative movement between sensor head and object, in particular the skin, between the acquisition of the two original initial images is almost completely ruled out or negligibly small.

During the acquisition of the images the sensor head is preferably in direct contact with the surface of the object to be examined, in particular the skin, which significantly reduces the probability of a relative movement. This is a particular advantage with acquisitions of images of the human or animal skin, since the same is generally elastic and adheres to the tip of the sensor head, particularly during the application of a gel, so that slight lateral movements or the slight tipping of the sensor head most often do not lead to a relative movement between skin and sensor head.

In the operating mode 3, in which static three-dimensional tomograms are acquired, a beat—as described above in detail—is generated between the detector sensitivity modulation on the one hand, and the interference signal to be captured on the other. As a result the distance between the individual sampling points in the depth direction is larger than in the operating mode 1, so that correspondingly fewer sample points, preferably between 6 and 10, in particular 8, are combined to maintain a cube-shaped three-dimensional image element (voxel).

FIG. 12 shows an example of an initial image (left) in comparison with a corresponding final image (right) that was obtained by means of the described interpolation. The final image is less noisy in contrast to the initial image, and appears therefore "softer" or "smoother". During comparisons in the interpretation of the images for diagnosis purposes it has turned out, in particular in the field of dermatology, that the relevant diagnostic information in each case can be obtained faster and more reliably from the final images obtained through trilinear interpolation. This applies in particular to cavities or inhomogeneities with a size of typically more than 10 μm.

The explanations provided above regarding the trilinear interpolation apply correspondingly also to a tricubic interpolation, where the initial values are not interpolated using a linear function, but instead using a cubic function.

5. System for Optical Coherence Tomography

FIG. 13 shows a schematic representation of a system 50 for implementing the inventive method for optical coherence tomography. The system 50 comprises a housing 51, entry devices in the form of a key pad 53, a computer mouse 54 as well as a foot switch device 55 that has a left, center and right foot switch 55l, 55m and 55r respectively. The housing 51 in the displayed example is designed to be mobile by being provided with rollers 56.

Furthermore a measuring head 57 is provided, which is connected to the housing 51 via a cable 58 or a cable hose or -pipe. The measuring head 57, in its idle position, is plugged into a measuring head holder provided on or in the housing 51, from which said measuring head can be removed during the acquisition of the OCT images, which in the figure is indicated by the measuring head 57, represented by a dashed line, and the cable 58, represented by a dashed line.

The system has a display device 52 in the form of a flat panel monitor that can display OCT images 60 and 61, which were captured by placing the measuring head 57 on an object, in particular the skin of a patient. In the example shown in the figure the first OCT image 60 concerns a depth section running substantially perpendicular to the surface of the object being examined, which depth section was acquired in the operating mode 1 described above, and the second OCT image 61 concerns a two-dimensional tomogram that runs substantially parallel to the surface of the object being examined, and that was acquired in the operating mode 2 described above.

In the area of the first OCT image 60 a straight line 62 is displayed on the display device 52, which straight line can be moved upward or downward in the direction of the indicated double arrow, for example by selecting a corresponding position of the straight line 62 relative to the first OCT image 60 with the aid of the entry devices 53, 54 and 55. The system 50 is configured in such a way that, corresponding to the selected location of the straight line 62 in the displayed first OCT image 60, a plane in the object being examined, running perpendicular to the displayed first OCT image 60, is determined automatically and a two-dimensional tomogram is acquired there, which is then displayed as the second OCT image 61.

The first OCT image 60 is preferably a so-called slice, while the second OCT image 61 preferably represents a so-called en-face image, which has been acquired in a plane corresponding to the straight line 62 in the first OCT image 60.

A depth selection display 63 in the form of a switch symbol, which is movable along a straight line, is furthermore displayed on the monitor of the display device 52, which switch symbol shows the depth that was selected through a selection of the location of the straight line 62 relative to the first displayed OCT image 60. Alternatively or in addition the depth can also be indicated in the form of numerical values.

One or several additional selection displays can furthermore be provided on the display device 52. In the displayed example a selection screen 64 is provided that shows one or several properties of the object to be examined. These properties are preferably selected and entered by an operator prior to the acquisition of corresponding OCT images. In the case of dermatological applications this concerns, for example, a parameter for the characterization of the moisture of the skin of the respective patient. In the corresponding selection screen 64 a corresponding switch symbol can then be moved continuously or in specified steps along a straight line between the positions "dry skin" on the left and "moist skin" on the right.

The interferometer 10 displayed in FIG. 1, including the optics 28 and the detector 30, is integrated in the measuring head 57. The light source 20, including the optics in the form of the two lenses 23 and 24 on the input side, is preferably integrated into the housing 51 of the system 50. The optical waveguide 26, which couples the light source 20 on the one hand and the interferometer 10 on the other with one another, is guided within the cable 58 from the housing 51 to the measuring head 57 in this case. In cable 58 electrical lines are furthermore guided that on the one hand serve the purpose of supplying power and controlling the measuring head 57, and on the other conduct the detector signals, which are generated during the capture of OCT images, of the detector 30 from the same into the housing 51, where they are supplied to a processing device (not displayed).

The measuring head 57, which in FIG. 13 is shown only heavily schematized, is displayed in detail in FIG. 14. A grip 57b is provided in the lower area of a measuring head housing 57a of the measuring head 57, which grip can be used by an operator to remove the measuring head 57 from the measuring head holder on or in the housing 51, or to plug said measuring head again into the measuring head holder, and to place said measuring head onto the object during the acquisition of OCT images and, if applicable, to guide said measuring head along said object. In this context the measuring head 57, with a contact surface 57c that is located on the front end of the measuring head housing 57a, is brought into contact with the object to be examined, in particular the skin of a patient.

In the center of the contact surface 57c a window 57d is provided, through which light from the sample arm 14 of the interferometer 10 (see FIG. 1) located in the measuring head 57 can pass, and can thereby irradiate the object to be examined. The light reflected and/or backscattered at different depths of the object reenters the sample arm 14 of the interferometer 10 through the window 57d and can there be captured and analyzed in the form of interference phenomena, as was already illustrated in detail above.

A status display device 57e, preferably in the form of an indicator light, is furthermore provided on the measuring head housing 57a, by means of which for example the readiness of the system 50 and/or the measuring head 57 for the capturing of OCT images is shown.

The cable 58, which can also be designed as a cable conduit or hose, is connected to the measuring head 57 in the area of the rear end of the measuring head housing 57a.

With the system 50 for optical coherence tomography described above, three- and two-dimensional cross section images of an object, in particular the human skin, can be acquired, where penetration depths into the human skin of up to approximately 1 mm can be reached, and the size of the surface of the skin area examined has typical dimensions of approximately 1.8×1.5 mm. Due to the infrared radiation that is used in the described system 50, with a preferred mean wavelength of approximately 1.3 µm, radiation exposure of the patient, such as for example during the use of x-rays, can be ruled out. The OCT images captured with the described system 50 furthermore have high resolution and permit a display of individual object structures on a scale down to 3 µm. Not least, the OCT images captured with the system 50 can be used for measuring the absolute geometric extent of the different structures, i.e. their size.

The system 50 has—even if not explicitly shown—a control device for the inventive control of the system 50, in particular the optical coherence tomography equipment, or the execution of the sequences described previously and hereinafter. The system furthermore comprises a processing device for the processing of different data, including the interpolation of initial image values described above. The control device and/or the processing device are preferably integrated into housing 51 of the system 50.

6. Workflows, Depth and Lateral Navigation

The functionality and the handling of the system 50 for optical coherence tomography are described hereinafter, by way of example, on the basis of typical and/or preferred sequences (so-called workflows). The advantages hereby achieved are also explained.

FIG. 15 shows the content of the monitor 70 of the display device in the administration mode, in which the system is automatically set after starting. A status display 71 in the form of a suitable symbol, for example a green disc, shows the readiness of the system. Preferably the readiness of the system, in particular for the acquisition of OCT images, is shown simultaneously through the activation of the status display 57e provided on measuring head 57. Hence, an operator has the opportunity of recognizing the readiness of the system solely on the basis of the status display 71 on the monitor 70, or on the basis of the status display 57e on the measuring head 57.

Information regarding the object to be examined, in particular regarding a patient, can be entered in an entry field 72. Preferably the system is hereby configured in such a way that a acquisition of OCT images is only possible when at least one item of the information requested in the entry field 72 has been entered, for example at least the last name of a patient.

The information entered in entry field 72, in particular the first and last name, patient identification number as well the data of birth, then appear—as illustrated as an example in FIG. 16—in the corresponding fields 72' in the upper area of the monitor display 70.

As soon as the measuring head 57 is removed from the measuring head holder that is located on or in the housing 51 of the system, the system starts automatically in the operating mode 1 (so-called slice mode). An optical gel is applied to the contact surface 57c of the measuring head 57 prior to bringing the contact surface 57c of the measuring head 57 in contact with the skin of the patient, which gel assures that, on the one hand, sharp index of refraction transitions between the skin and the window 57d of the measuring head 57 are bridged (so-called index matching) and, on the other hand, irregularities on the skin surface are evened out. Preferably the amount of the optical get applied to the contact surface 57c is, depending on the application case, between approximately 2 µl and 10 µl.

After application of the gel, the contact surface 57c of the measuring head 57 is pressed against the patient's skin area to be examined and moved back and forth slightly over the skin area by an operator in order to achieve an optimal distribution of the optical gel.

Since the system is already in the slice mode immediately after the removal of the measuring head 57 from the measuring head holder, a slice image 73 is captured immediately after a contact with the skin area to be examined is established, and displayed in the area of the center of the monitor 70, as illustrated in FIG. 17. A display 74 is provided in the right area of the monitor 70, where the skin type of the skin being examined in each case is set or shown. Preferably this relates to a parameter that characterizes the moisture content of the skin area being examined. A corresponding switch symbol can in this case be moved by the operator, in steps or also continuously, on a scale between "dry skin" and "moist skin". The selection of this parameter specifies the ratio of the speeds with which the reference mirror 16 and the lens or lenses of the sample objective 14a (see FIG. 1 as well as FIGS. 6a and 6b) move, in order to assure an optimal focus tracking.

For the acquisition of the slice image 73 that is displayed in FIG. 17 a position of the switch symbol of the display 74 was selected that is located slightly above the center of the scale, corresponding to a more moist skin. The result is a bright and relatively high-contrast slice image 73.

In contrast, the slice image 75 displayed in FIG. 18 was captured with a parameter setting where the switch symbol of the display 74 is located beneath the center of the scale, which corresponds to a more dry skin. The contrast of the slice image 75 captured with this setting is significantly lower compared with the slice image 73 shown in FIG. 17, as can be clearly seen in FIG. 18. The reason is that the focus of the sample objective 14 was not or not always positioned in the range of the corresponding coherence gate during the acquisition of the slice image 75 at the different depths of the skin. For further details reference is made to the explanations above in the context of focus tracking.

Proceeding from a slice image 73 (see FIG. 17) obtained with the optimal setting of the parameter corresponding to the skin moisture, actuation of a corresponding switch, preferably by means of a prolonged pressing of the center foot switch 55m (see FIG. 13), enables switching from the slice mode to the en-face mode, in which—as illustrated in FIG. 19—the slice image 73 is displayed scaled-down (so-called thumbnail) in the right area of the monitor 70, and simultaneously an en-face image 76 that was acquired in the operating mode 2, the so-called en-face mode, is shown in the center area of the monitor 70. The displayed en-face image 76 is preferably a real time image that is being acquired and updated at a repetition rate of at least one image per second. The scaled-down display of the slice image 73 in the right area of the monitor 70, on the other hand, is a static image, corresponding, for example, to the last slice image acquired and displayed in the slice mode (see FIG. 17) in real time.

The depth of the skin at which the displayed en-face image 76 is acquired can be selected by the operator via a depth selection switch 77 shown on the monitor 70, by actuating a corresponding switch symbol, for example using the computer mouse 54, the key pad 53 and/or the foot switch device 55 (see FIG. 13). Preferably the setting or selection of a specific depth takes place via the left foot switch 55l, which is designed as a rocker switch and which initiates a change in depth toward greater or smaller depth via actuation of the rocker toward the front or the back.

The selection of a certain depth on the basis of a displayed first OCT image, as described above, at which depth a second OCT image is acquired, is also referred to as depth navigation in the context of the illustration of the inventive system and method.

Preferably the system is configured such that a selection of the depth at which an en-face image is to be captured can be tracked with an accuracy as low as one micrometer. Basically it is possible that the size of the steps at which depth navigation is performed is specified. As an example, the specification can be made prior to the start of an examination, i.e. the acquisition of several OCT images of a patient, that the selection of the respective depth for en-face images is to take place in steps of 5 µm. In this manner the depth navigation can be adapted individually to the respective purpose of diagnosis.

The previously described selection of a certain depth for the acquisition of an en-face image is explained hereinafter in more detail on the basis of the monitor displays shown in FIGS. 20 to 23.

FIG. 20 shows an en-face image 80 that was acquired at a depth between the window 57d positioned on the measuring head 57, which window can be recognized in the form of a horizontal line 79 in the corresponding slice image 81, and the skin surface, and for that reason shows only a cross section of the gel layer that is located between the window 57d and the skin. The depth set in this example is shown by means of a horizontal straight line 78 marked in slice image 81, which is displayed scaled-down. Furthermore the selected or set depth can also be obtained from the respective position of the depth selection switch 77 and/or a corresponding numerical value display.

FIG. 21 shows an en-face image 32 that was acquired in a plane that is located in the upper most region of the skin surface, as can be recognized from the position of the straight line 78 that serves as a depth display, relative to the slice image 81 that is displayed scaled-down. The region between the straight line 78 on the one hand and the horizontal line 79 on the other, which is due to light reflections on the window 57d of the measuring head 57, corresponds to the gel layer located between the window 57d and the skin.

By actuating the left foot switch 55l or the corresponding switch symbol in the depth selection display 77, for example with the aid of the computer mouse 54, the straight line 78 can be moved (see double arrow) relative to the slice image 81, which is displayed scaled-down, with the result that planes located at different depths in the skin can be selected, in which corresponding en-face images are acquired and shown on the monitor view.

The principle of depth navigation is further illustrated in the right lower part of FIG. 21 on the basis of a plane that is marked in a skin model, said plane running substantially parallel to the skin surface and can be moved to different depths in the direction of the double arrow.

FIG. 22 shows, as an example, an additional en-face image 83 that was acquired at another depth of the examined skin area. The plane of the obtained en-face image 83 is now completely within the examined skin area, as can be recognized from the position of the straight line 78 relative to the slice image 81. Moreover, the statements in connection with the FIGS. 20 and 21 apply correspondingly.

FIG. 23 shows an advantageous use of the depth navigation described above for the detection of diagnostically relevant information. As an example, the depth for the acquisition of an en-face image 84 can be selected in the displayed slice image 81 via the selection of the location of the straight line 78, in order to, for example, further analyze a cavity 85, which is suspected on the basis of the slice image 81, in a corresponding plane of the en-face image 84, which plane runs perpendicular to the slice image 81.

Additional aspects of the described sequence during the acquisition of OCT image with the inventive system are explained hereinafter in more detail.

In the right area of the monitor 70, which is shown in FIG. 24, a scaled-down slice image 85 is displayed that was acquired in the slice mode and stored in a non-volatile memory of the system, for example a hard disk memory, via actuation of a corresponding switch, preferably via briefly pressing the center foot switch 55m (see FIG. 13).

A depth navigation, as it was explained in detail in the context of the FIGS. 19 to 23, can be performed on the basis of the stored and displayed slice image 85. Preferably the system is hereby configured in such a manner that an additional slice image 86 is automatically generated and displayed in the right area of the monitor 70, if the slice image stored last, in this case the slice image 85, is already older than a specified time duration, for example 10 seconds, during the switch from the slice mode to the en-face mode. This case is shown in the example displayed in FIG. 24, where the slice image 85 was acquired at a first time point and stored after entry of a corresponding operator command, and the switch to the en-face mode was only made after a time duration of more than 10 seconds after the acquisition and storing of the slice image 85. In this case an additional slice image 86 was acquired immediately after the switch to the en-face mode, stored temporarily, for example in a volatile memory of the system, and displayed scaled-down in the right area of the monitor 70, where a straight line 78 is superimposed in the region of the OCT image 86 for performing the depth navigation described above, on the basis of which straight line an operator can recognize and control at what depth in the object, in each case, a corresponding en-face image 87 is acquired and displayed, preferably in the center area of the monitor 70.

This configuration of the system assures that the depth navigation previously described is always performed on a most current slice image, so that possible relative movements between the measuring head on the one hand and the object on the other, including movements within the object itself, can be taken into account, and can therefore not affect the reliability of the acquisition of OCT images, in particular en-face images, negatively.

The adjustable time interval between the acquisition and storing of a slice image on the one hand, and the change from slice mode to the en-face mode on the other, where due to the time interval being exceeded an additional slice image is acquired, temporarily stored and shown on the monitor 70, was set to 10 seconds in the displayed example. Basically it is however also possible to select this time interval to be significantly shorter, for example 5 seconds, if the type of respective examination requires this. This can be the case, for example, if the measuring head, due to larger movements of the object, in particular a patient, can not be maintained sufficiently long in a fixed position relative to the object. On the other hand it is however also possible to specify longer time intervals, for example 15 seconds, when, for example, the object to be examined remains stationary for a longer time interval and a fixed relative position between measuring head and object can be assured.

FIG. 25 shows a monitor view 70 after the switch from the en-face mode, whose monitor display is displayed as an example in FIG. 24, back to the slice mode. In the right area of the monitor view 70 the slice image 85 is shown, which in this case is permanently stored due to an operator command, not, however, the slice image 86 (see FIG. 24), which is only temporarily stored for navigation purposes. Furthermore the en-face image 87 that was acquired and shown last in the en-face mode is displayed in a scaled-down form after the switch to the slice mode.

A currently acquired slice image 88 is displayed in the center area of the monitor 70. Analogously to the depth navigation described above, the system is configured in such a way that a plane, which is perpendicular to the plane of the displayed en-face image 87, can also be selected in the en-face image 87, which is displayed scaled-down, with the aid of an additionally displayed straight line 89, in which plane the slice image 88 is acquired.

The selection, which is performed on the basis of an en-face image, of slice image planes, which run substantially parallel to the light impinging on the object and perpendicular to the skin surface or to the plane of the en-face image, can also be referred to as lateral navigation. Moreover, the statements above in connection with the depth navigation apply correspondingly.

The principle of lateral navigation is further illustrated in the right lower part of FIG. 25 on the basis of a plane that is marked in a skin model, which plane runs substantially perpendicular to the skin surface and can be moved laterally in the direction of the double arrow.

In the monitor view 70 shown in FIG. 25 a slice image 88' is furthermore displayed in the right area, which was stored in the currently selected slice mode via a corresponding operator selection command. Furthermore a 3D symbol 90 is shown that indicates that in the meantime a three-dimensional tomogram acquired in operating mode 3 was also acquired and stored.

7. Image Viewing and Administration Mode

After the completion of the acquisition of one or a plurality of, possibly different, OCT images, the measuring head 57 is plugged again into the measuring head holder located on the housing 51 of the system 50, whereupon the monitor display 70—as shown in FIG. 26—transitions automatically into an image viewing mode, in which the operator can select the displayed and stored OCT images 85, 87, 88' and 90, which are displayed scaled-down in the right area of monitor 70, wherein each selected scaled-down image is displayed enlarged in the center area of the monitor 70.

In the case where a three-dimensional tomogram 90 is selected, a perspective rendition of the acquired three-dimensional tomogram can be provided in the center area of the monitor 70. For certain diagnostic applications it can be advantageous, however, to display, in each case, a slice image 91, which originates from the three-dimensional tomogram, and an en-face image 92 together and enlarged in the center area of the monitor 70, as shown as an example in FIG. 26. It is hereby advantageous to use the principle of depth and lateral navigation, as described above, in this case also, wherein corresponding straight lines 93 and 94 are superimposed on the displayed slice and en-face images 91 and 92 respectively. The user can specify the plane of each displayed slice image 91 via the selection of a straight line 93 or 94 as well as via the selection of the location of the selected straight line 93 or 94 in the area of the en-face image 92. Furthermore a selection of a plane of the en-face image that is to be shown and that originates from the three-dimensional tomogram can take place via selecting and sliding of the straight line 93 in the area of the slice image 91.

The capability of entering comments in the image viewing mode is illustrated on the basis of the monitor view 70 displayed in FIG. 27. To this end the operator initially selects an OCT image for commenting, which in the displayed example is the slice image 85, and then opens a corresponding comment field 97 that is associated with this image, in which comment field then any comments can be entered in the form of free text. Furthermore a general comment field 96 is opened, in which a comment regarding the performed examination can be entered which is associated with the entirety of the OCT images 85, 87, 88' and 90 acquired during this examination and which is shown during retrievals of at least one of these images together with the retrieved image. The slice image 85, which is selected and displayed scaled-down in the right area of the monitor 70, is displayed enlarged in the center of the monitor 70 shown in FIG. 27.

After completion of the analysis and, if applicable, the commenting regarding to the OCT images acquired during the examination, an administration mode of the system 50 can be selected in which the performed examination is shown in monitor view 70, as displayed in FIG. 28, in the form of, respectively, one line 98. By selecting the corresponding line 98, the operator can again switch into the image viewing mode and analyze and, if applicable, enter comments for the acquired OCT images.

An examination report of the performed examination, as shown as an example in FIG. 29, can be generated—automatically or after completion of the examination or after a user command. In the examination report, which is preferably created in the HTML format, the patient information that was entered prior to the examination, the OCT images 85, 87, 88' and 90 that were acquired during the examination and stored in response to a user command, as well as the respectively entered comments 96 and 97 are compiled in the form of an overview.

8. Additional Inventive Aspects of the System and Method

The OCT system and method previously described in more detail has individual features or feature combinations that make the system and method more straightforward, quicker and more reliable with regard to handling and image acquisition, without all of the features listed in the preamble and/or characterizing portion of the independent claims being hereby imperatively required. These features or feature combinations are likewise considered an invention.

In particular, a system for optical coherence tomography is considered an invention with at least one interferometer for the emission of light for the irradiation of an object, and a detector for the detection of light that is reflected and/or backscattered from the object, wherein the system is characterized by one or a plurality of features, which were previously described in more detail, in particular in the sections 1 to 7 and/or in connection with the FIGS. 1 to 29. The method corresponding to this system is likewise considered an invention.

Furthermore, a method for optical coherence tomography is considered an invention, where a first image is acquired, in particular in real time, in the region of a first plane of an object by means of an optical coherence tomography equipment, and the first image is displayed on a display device, in particular as a real time image, wherein the method is characterized by one or a plurality of features, which were previously described in more detail, in particular in the sections 1 to 7 and/or in connection with the FIGS. 1 to 29. The system corresponding to this method is likewise considered an invention.

The invention claimed is:

1. A method for performing optical coherence tomography, the method comprising the steps of:
   successive sampling of an interference pattern at different depths within a depth range of an object to obtain a plurality of original initial image values at the different depths within the depth range of the object using optical coherence tomography equipment including a reference mirror, the successive sampling of the interference pattern being performed by successively detecting light reflected or backscattered from the object during a movement of the reference mirror; and
   obtaining a plurality of initial image values by combining at least two of the plurality of original initial image values, which were obtained at the different depths within the depth range of the object, to one initial image value, wherein the plurality of initial image values are located on a three-dimensional regular grid and adjacent initial image values are equally spaced apart in all three spatial dimensions, and the plurality of initial image values define at least two two-dimensional images of the object in planes of the object that are spaced apart from one another; and
   interpolating the plurality of initial image values of the at least two two-dimensional initial images in three-dimensional space by at least one of trilinear interpolation, triquadratic interpolation, tricubic interpolation, and multi-variate interpolation in the three-dimensional regular grid on which the plurality of initial image values of the at least two two-dimensional initial images are located to obtain interpolation values that form a two-dimensional final image.

2. The method according to claim 1, wherein the plurality of initial image values of the at least two two-dimensional initial images are interpolated by at least one of the trilinear interpolation and the tricubic interpolation.

3. The method according to claim 1, wherein the at least two two-dimensional initial images are real time images that are acquired at a rate of at least one image per second.

4. The method according to claim 1, wherein, in a first operating mode, acquiring the at least two two-dimensional initial images in planes of the object that are spaced apart from one another and light reflected or backscattered by the object is detected only by a partial surface of a spatially resolving detector of the optical coherence tomography equipment; and
   changing an optical distance of a reflector from a beam splitter of the optical coherence tomography equipment by an optical path that is larger than a mean wavelength $\lambda_0$ of light injected into the optical coherence tomography equipment.

5. The method according to claim 1, wherein, in a second operating mode, acquiring the at least two two-dimensional initial images of the object in two planes of the object that are spaced apart from one another during changing of an optical distance of a reflector from a beam splitter of the optical coherence tomography equipment; and
   detecting the light reflected from the object a plurality of times by detector elements of a detector; wherein
   the changing of the optical distance of the reflector from the beam splitter is at most forty times a mean wavelength $\lambda_0$ of light injected into the optical coherence tomography equipment.

6. The method according to claim 5, wherein the two planes extend at different depths in the object above and below a mean depth in the object.

7. The method according to claim 6, wherein the two planes have a same distance from the mean depth.

8. The method according to claim 6, wherein the mean depth or the different, respectively, of the planes extending above or below the mean depth in the object are set by the optical distance of the reflector from the beam splitter.

9. The method according to claim 8, wherein the changing of the optical distance of the reflector from the beam splitter of the optical coherence tomography equipment is changed by an optical path that is larger than the mean wavelength $\lambda_0$ of the light injected into the optical coherence tomography equipment.

10. The method according to claim 6, wherein a spacing of the two planes relative to one another corresponds to a same spacing of the plurality of initial image values in all three spatial dimensions.

11. The method according to claim 1, wherein spacing of two planes of the at least two two-dimensional images planes relative to one another corresponds to a same spacing of the plurality of initial image values in all three spatial dimensions.

12. The method according to claim 1, wherein the depth range of the object in the at least one dimension corresponds to a resolution of the optical coherence tomography equipment.

13. The method according to claim 1, wherein the at least two two-dimensional initial images of the object are acquired in planes of the object that extend parallel to one another.

14. The method according to claim 1, wherein the combining step reduces a number of the plurality of initial image values in a direction of the depth range of the object.

15. The method according to claim 1, wherein the depth range of the object in the at least one dimension corresponds to an axial resolution or a depth resolution of the optical coherence tomography equipment.

16. A system for performing optical coherence tomography, the system comprising:

an optical coherence tomography equipment including an interferometer including a reference mirror, a light source that generates light and injects the light into the interferometer to illuminate an object, and a detector that detects light that is reflected or backscattered from the object; and a processor that:

obtains a plurality of initial image values using the optical coherence tomography equipment by combining at least two of a plurality of original initial image values, which were obtained by successive sampling of an interference pattern at different depths within a depth range of the object, into one initial image value, the successive sampling of the interference pattern being performed by successively detecting the light reflected or backscattered from the object during a movement of the reference mirror, wherein the plurality of initial image values are located on a three-dimensional regular grid and adjacent initial image values are equally spaced apart in all three spatial dimensions, and the plurality of initial image values define at least two two-dimensional images of the object in planes of the object that are spaced apart from one another; and that interpolates the plurality of initial image values of the at least two two-dimensional initial images in three-dimensional space by at least one of trilinear interpolation, triquadratic interpolation, tricubic interpolation, and multi-variate interpolation in the three-dimensional regular grid on which the plurality of initial image values of the at least two two-dimensional initial images are located to obtain interpolation values that form a two-dimensional final image.

17. The system according to claim 16, wherein the at least two two-dimensional initial images of the object are acquired in planes of the object that extend parallel to one another.

* * * * *